US012673005B2

(12) United States Patent (10) Patent No.: US 12,673,005 B2

Fangrow (45) Date of Patent: Jul. 7, 2026

(54) MEDICAL CONNECTORS CONFIGURED TO RECEIVE EMITTERS OF THERAPEUTIC AGENTS

(71) Applicant: ICU Medical, Inc., San Clemente, CA (US)

(72) Inventor: Thomas F. Fangrow, San Clemente, CA (US)

(73) Assignee: ICU Medical, Inc., San Clemente, CA (US)

( * ) Notice: Subject to any disclaimer, the term of this patent is extended or adjusted under 35 U.S.C. 154(b) by 874 days.

(21) Appl. No.: 18/066,670

(22) Filed: Dec. 15, 2022

(65) Prior Publication Data

US 2023/0144160 A1 May 11, 2023

Related U.S. Application Data

(63) Continuation of application No. 16/694,564, filed on Nov. 25, 2019, now Pat. No. 11,559,467, which is a
(Continued)

(51) Int. Cl.
*A61J 1/20* (2006.01)
*A61M 5/14* (2006.01)
(Continued)

(52) U.S. Cl.
CPC ........... *A61J 1/2065* (2015.05); *A61J 1/2089* (2013.01); *A61J 1/2096* (2013.01);
(Continued)

(58) Field of Classification Search
CPC ...... A61J 1/2065; A61J 1/2089; A61J 1/2096; A61M 5/1409; A61M 5/32; A61M 39/10; A61M 39/26
See application file for complete search history.

(56) References Cited

U.S. PATENT DOCUMENTS 382,297 A 5/1888 Fry
559,697 A 5/1896 Tiugti et al.
(Continued)

FOREIGN PATENT DOCUMENTS

AU 2014 216 480 8/2015
AU 2013 224680 9/2016
(Continued)

OTHER PUBLICATIONS

ICU Medical SwabPack, top-access bag of disinfecting caps for needlefree connectors, on sale at least as early as Jan. 2012.
(Continued)

*Primary Examiner* — Philip R Wiest
(74) *Attorney, Agent, or Firm* — Knobbe, Martens, Olson & Bear, LLP

(57) ABSTRACT

In some embodiments, a medical fluid connector is configured to receive an emitter of therapeutic agents to be emitted into a fluid pathway within the connector, the medical fluid connector comprising a proximal female end, an intermediate region, a distal male end, and a fluid pathway extending from the proximal female end, through the intermediate region, to the distal male end. A retaining structure is positioned within the intermediate region. The retaining structure is configured to securely receive an emitter of one or more therapeutic agents in a position and orientation where the fluid pathway is configured to convey fluid moving longitudinally through the fluid pathway directly into a proximal region of the emitter, around one or more lateral surfaces of the emitter, and toward the distal male end.

21 Claims, 14 Drawing Sheets

Related U.S. Application Data continuation of application No. 15/726,838, filed on Oct. 6, 2017, now Pat. No. 10,524,982, which is a continuation of application No. PCT/US2016/030844, filed on May 4, 2016.

(60) Provisional application No. 62/212,473, filed on Aug. 31, 2015, provisional application No. 62/159,130, filed on May 8, 2015.

(51) Int. Cl.
| | | |
|---|---|---|
| *A61M 5/32* | (2006.01) | |
| *A61M 39/10* | (2006.01) | |
| *A61M 39/26* | (2006.01) | |

(52) U.S. Cl.
CPC ............ *A61M 5/1409* (2013.01); *A61M 5/32* (2013.01); *A61M 39/10* (2013.01); *A61M 39/26* (2013.01); *A61M 5/3294* (2013.01)

(56) References Cited

U.S. PATENT DOCUMENTS

| | | | |
|---|---|---|---|
| 877,946 | A | 2/1908 | Overton |
| 975,939 | A | 11/1910 | Edwards et al. |
| 1,445,642 | A | 2/1923 | O'Neill |
| 1,793,068 | A | 2/1931 | Dickinson |
| 2,098,340 | A | 11/1937 | Henahan |
| 2,436,297 | A | 2/1948 | Guarnaschelli |
| 2,457,052 | A | 12/1948 | Clair |
| 2,771,644 | A | 11/1956 | Martin |
| 2,842,382 | A | 7/1958 | Franck |
| 2,968,497 | A | 1/1961 | Treleman |
| 3,127,892 | A | 4/1964 | Bellamy, Jr. et al. |
| 3,262,448 | A | 7/1966 | Ring et al. |
| 3,270,743 | A | 9/1966 | Gingras |
| 3,301,392 | A | 1/1967 | Eddingfield |
| 3,304,047 | A | 2/1967 | Martin |
| 3,334,860 | A | 8/1967 | Bolton, Jr. |
| 3,411,665 | A | 11/1968 | Blum |
| 3,460,742 | A | 8/1969 | Langdon |
| 3,484,121 | A | 12/1969 | Quinton |
| 3,485,416 | A | 12/1969 | Fohrman |
| 3,538,950 | A | 11/1970 | Porteners |
| 3,595,241 | A | 7/1971 | Sheridan |
| 3,604,582 | A | 9/1971 | Boudin |
| 3,707,972 | A | 1/1973 | Villari et al. |
| 3,729,031 | A | 4/1973 | Baldwin |
| 3,882,858 | A | 5/1975 | Klemm |
| 3,977,401 | A | 8/1976 | Pike |
| 3,977,517 | A | 8/1976 | Kadlecik et al. |
| 3,987,930 | A | 10/1976 | Fuson |
| 3,993,066 | A | 11/1976 | Virag |
| 4,041,934 | A | 8/1977 | Genese |
| 4,046,889 | A | 9/1977 | Ondetti et al. |
| 4,052,511 | A | 10/1977 | Cushman et al. |
| 4,053,052 | A | 10/1977 | Jasper |
| 4,053,651 | A | 10/1977 | Ondetti et al. |
| 4,066,067 | A | 1/1978 | Micheli |
| 4,076,285 | A | 2/1978 | Martinez |
| 4,078,686 | A | 3/1978 | Karesh et al. |
| 4,079,738 | A | 3/1978 | Dunn et al. |
| 4,095,810 | A | 6/1978 | Kulle |
| 4,113,751 | A | 9/1978 | Arnold |
| 4,121,585 | A | 10/1978 | Becker, Jr. |
| 4,129,571 | A | 12/1978 | Ondetti et al. |
| 4,133,441 | A | 1/1979 | Mittleman et al. |
| 4,143,853 | A | 3/1979 | Abramson |
| 4,150,845 | A | 4/1979 | Kopacz et al. |
| 4,154,840 | A | 5/1979 | Ondetti et al. |
| 4,154,960 | A | 5/1979 | Ondetti et al. |
| 4,192,443 | A | 3/1980 | McLaren |
| 4,194,509 | A | 3/1980 | Pickering et al. |
| 4,195,632 | A | 4/1980 | Parker et al. |
| 4,233,982 | A | 11/1980 | Bauer et al. |
| 4,243,035 | A | 1/1981 | Barrett |
| 4,245,635 | A | 1/1981 | Kontos |
| 4,264,664 | A | 4/1981 | Kunz |
| 4,280,632 | A | 7/1981 | Yuhara |
| 4,294,370 | A | 10/1981 | Toeppen |
| 4,317,446 | A | 3/1982 | Ambrosio et al. |
| 4,324,239 | A | 4/1982 | Gordon et al. |
| 4,325,368 | A | 4/1982 | Kaemmerer |
| 4,331,783 | A | 5/1982 | Stoy |
| 4,334,551 | A | 6/1982 | Pfister |
| 4,335,756 | A | 6/1982 | Sharp et al. |
| 4,337,327 | A | 6/1982 | Stoy |
| 4,340,049 | A | 7/1982 | Munsch |
| 4,340,052 | A | 7/1982 | Dennehey et al. |
| 4,354,490 | A | 10/1982 | Rogers |
| 4,369,294 | A | 1/1983 | Stoy |
| 4,370,451 | A | 1/1983 | Stoy |
| 4,379,458 | A | 4/1983 | Bauer et al. |
| 4,379,874 | A | 4/1983 | Stoy |
| 4,384,589 | A | 5/1983 | Morris |
| 4,387,879 | A | 6/1983 | Tauschinski |
| 4,390,016 | A | 6/1983 | Riess |
| 4,397,442 | A | 8/1983 | Larkin |
| 4,402,691 | A | 9/1983 | Rosenthal et al. |
| 4,405,312 | A | 9/1983 | Gross et al. |
| 4,417,890 | A | 11/1983 | Dennehey et al. |
| 4,420,589 | A | 12/1983 | Stoy |
| 4,427,126 | A | 1/1984 | Ostrowsky |
| 4,430,073 | A | 2/1984 | Bemis et al. |
| 4,432,764 | A | 2/1984 | Lopez |
| 4,432,766 | A | 2/1984 | Bellotti et al. |
| 4,436,125 | A | 3/1984 | Blenkush |
| 4,439,179 | A | 3/1984 | Lueders et al. |
| 4,439,184 | A | 3/1984 | Wheeler |
| 4,440,207 | A | 4/1984 | Genatempo et al. |
| 4,444,310 | A | 4/1984 | Odel |
| 4,446,967 | A | 5/1984 | Halkyard |
| 4,447,419 | A | 5/1984 | Quadro |
| 4,457,749 | A | 7/1984 | Bellotti et al. |
| 4,461,368 | A | 7/1984 | Plourde |
| 4,461,896 | A | 7/1984 | Portlock |
| 4,480,940 | A | 11/1984 | Woodruff |
| 4,507,111 | A | 3/1985 | Gordon et al. |
| 4,511,359 | A | 4/1985 | Vaillancourt |
| 4,534,764 | A | 8/1985 | Mittleman et al. |
| 4,538,836 | A * | 9/1985 | Krutten ................ A61M 39/10 |
| | | | 285/423 |
| 4,559,043 | A | 12/1985 | Whitehouse |
| 4,568,675 | A | 2/1986 | Bush et al. |
| 4,585,758 | A | 4/1986 | Huang et al. |
| 4,602,042 | A | 7/1986 | Chantler et al. |
| 4,610,469 | A | 9/1986 | Wolff-Mooij |
| 4,619,640 | A | 10/1986 | Potolsky et al. |
| 4,623,332 | A | 11/1986 | Lindmayer et al. |
| 4,624,664 | A | 11/1986 | Peluso et al. |
| 4,626,545 | A | 12/1986 | Taub |
| 4,629,159 | A | 12/1986 | Wellenstam |
| 4,631,188 | A | 12/1986 | Stoy |
| 4,642,091 | A | 2/1987 | Richmond |
| 4,660,803 | A | 4/1987 | Johnston et al. |
| 4,662,878 | A | 5/1987 | Lindmayer |
| 4,666,057 | A | 5/1987 | Come et al. |
| 4,666,427 | A | 5/1987 | Larsson et al. |
| 4,671,306 | A | 6/1987 | Spector |
| 4,671,412 | A | 6/1987 | Gatten |
| 4,681,886 | A | 7/1987 | Haugwitz et al. |
| 4,692,458 | A | 9/1987 | Ryan et al. |
| 4,692,459 | A | 9/1987 | Ryan et al. |
| 4,700,744 | A | 10/1987 | Rutter et al. |
| 4,703,762 | A | 11/1987 | Rathbone et al. |
| 4,705,790 | A | 11/1987 | Hubele et al. |
| 4,723,603 | A | 2/1988 | Plummer |
| 4,728,075 | A | 3/1988 | Paradis |
| 4,728,321 | A | 3/1988 | Chen |
| 4,738,668 | A | 4/1988 | Bellotti et al. |
| 4,745,950 | A | 5/1988 | Mathieu |
| 4,747,502 | A | 5/1988 | Luenser |
| 4,748,160 | A | 5/1988 | Bennion et al. |
| 4,752,983 | A | 6/1988 | Grieshaber |

(56) References Cited

U.S. PATENT DOCUMENTS

| | | | |
|---|---|---|---|
| 4,769,013 A | 9/1988 | Lorenz et al. | |
| 4,774,964 A | 10/1988 | Bonaldo | |
| 4,774,965 A | 10/1988 | Rodriguez et al. | |
| 4,778,447 A | 10/1988 | Velde et al. | |
| 4,781,702 A | 11/1988 | Herrli | |
| 4,799,926 A | 1/1989 | Haber | |
| 4,804,015 A | 2/1989 | Albinsson | |
| 4,808,158 A | 2/1989 | Kreuzer et al. | |
| 4,810,241 A | 3/1989 | Rogers | |
| 4,811,847 A | 3/1989 | Reif et al. | |
| 4,813,933 A | 3/1989 | Turner | |
| 4,816,024 A | 3/1989 | Sitar et al. | |
| 4,834,271 A | 5/1989 | Litwin | |
| 4,862,913 A | 9/1989 | Wildfang | |
| 4,874,366 A | 10/1989 | Zdeb et al. | |
| 4,883,483 A | 11/1989 | Lindmayer | |
| 4,889,255 A | 12/1989 | Schiemann et al. | |
| 4,894,056 A | 1/1990 | Bommarito | |
| 4,898,580 A | 2/1990 | Crowley | |
| 4,915,687 A | 4/1990 | Sivert | |
| 4,917,669 A | 4/1990 | Bonaldo | |
| 4,919,658 A | 4/1990 | Badia | |
| 4,927,019 A | 5/1990 | Haber et al. | |
| 4,935,010 A | 6/1990 | Cox et al. | |
| 4,941,873 A | 7/1990 | Fischer | |
| 4,950,260 A | 8/1990 | Bonaldo | |
| 4,957,637 A | 9/1990 | Cornell | |
| 4,963,132 A | 10/1990 | Gibson | |
| D313,277 S | 12/1990 | Haining | |
| D314,050 S | 1/1991 | Sone | |
| 4,983,161 A | 1/1991 | Dadson et al. | |
| 4,985,017 A | 1/1991 | Theeuwes | |
| 4,989,733 A | 2/1991 | Patry | |
| 4,991,629 A | 2/1991 | Ernesto et al. | |
| 4,997,371 A | 3/1991 | Fischer | |
| 4,999,210 A | 3/1991 | Solomon et al. | |
| 5,002,964 A | 3/1991 | Loscalzo | |
| 5,006,114 A | 4/1991 | Rogers et al. | |
| 5,015,238 A | 5/1991 | Solomon et al. | |
| 5,019,096 A | 5/1991 | Fox, Jr. et al. | |
| 5,021,059 A | 6/1991 | Kensey et al. | |
| 5,024,657 A | 6/1991 | Needham et al. | |
| 5,025,001 A | 6/1991 | Loscalzo et al. | |
| 5,026,359 A | 6/1991 | Burroughs | |
| 5,031,622 A | 7/1991 | LaHaye | |
| 5,033,961 A | 7/1991 | Kandler et al. | |
| 5,047,021 A | 9/1991 | Utterberg | |
| 5,049,139 A | 9/1991 | Gilchrist | |
| 5,059,186 A | 10/1991 | Yamamoto et al. | |
| 5,065,783 A | 11/1991 | Ogle, II | |
| 5,070,885 A | 12/1991 | Bonaldo | |
| 5,071,411 A | 12/1991 | Hillstead | |
| 5,071,413 A | 12/1991 | Utterberg | |
| 5,098,385 A | 3/1992 | Walsh | |
| 5,108,376 A | 4/1992 | Bonaldo | |
| 5,122,123 A | 6/1992 | Vaillancourt | |
| 5,127,626 A | 7/1992 | Hilal et al. | |
| 5,129,824 A | 7/1992 | Keller | |
| 5,139,483 A | 8/1992 | Ryan | |
| 5,143,104 A | 9/1992 | Iba et al. | |
| 5,147,333 A | 9/1992 | Raines | |
| 5,154,703 A | 10/1992 | Bonaldo | |
| 5,154,920 A | 10/1992 | Flesher et al. | |
| 5,184,742 A | 2/1993 | DeCaprio et al. | |
| 5,190,534 A | 3/1993 | Kendell | |
| 5,195,957 A | 3/1993 | Tollini | |
| RE34,223 E | 4/1993 | Bonaldo | |
| 5,199,948 A | 4/1993 | McPhee | |
| 5,201,725 A | 4/1993 | Kling | |
| 5,203,775 A | 4/1993 | Frank et al. | |
| 5,205,820 A | 4/1993 | Kriesel | |
| 5,205,821 A | 4/1993 | Kruger et al. | |
| 5,207,706 A | 5/1993 | Menaker | |
| 5,211,634 A | 5/1993 | Vaillancourt | |
| 5,212,204 A | 5/1993 | Keefer et al. | |
| 5,215,537 A | 6/1993 | Lynn et al. | |
| 5,240,675 A | 8/1993 | Wilk et al. | |
| 5,242,421 A | 9/1993 | Chan | |
| 5,242,425 A | 9/1993 | White et al. | |
| 5,246,011 A | 9/1993 | Caillouette | |
| 5,250,550 A | 10/1993 | Keefer et al. | |
| 5,251,873 A | 10/1993 | Atkinson et al. | |
| D342,134 S | 12/1993 | Mongeon | |
| 5,269,771 A | 12/1993 | Thomas et al. | |
| 5,278,192 A | 1/1994 | Fung et al. | |
| 5,281,206 A | 1/1994 | Lopez | |
| 5,284,475 A | 2/1994 | Mackal | |
| 5,295,657 A | 3/1994 | Atkinson | |
| 5,297,310 A | 3/1994 | Cox et al. | |
| 5,301,686 A | 4/1994 | Newman | |
| 5,304,130 A | 4/1994 | Button | |
| 5,306,243 A | 4/1994 | Bonaldo | |
| 5,312,377 A | 5/1994 | Dalton | |
| 5,324,270 A | 6/1994 | Kayan et al. | |
| 5,324,647 A | 6/1994 | Rubens et al. | |
| 5,330,235 A | 7/1994 | Wagner et al. | |
| 5,330,426 A * | 7/1994 | Kriesel | A61M 5/2429 604/82 |
| 5,330,450 A | 7/1994 | Lopez | |
| 5,330,899 A | 7/1994 | Devaughn et al. | |
| 5,337,730 A | 8/1994 | Maguire | |
| 5,344,414 A | 9/1994 | Lopez et al. | |
| 5,352,410 A | 10/1994 | Hansen et al. | |
| 5,354,267 A | 10/1994 | Niermann et al. | |
| 5,356,396 A | 10/1994 | Wyatt et al. | |
| 5,360,413 A | 11/1994 | Leason et al. | |
| 5,366,505 A | 11/1994 | Farber | |
| 5,366,997 A | 11/1994 | Keefer et al. | |
| 5,370,614 A | 12/1994 | Amundson et al. | |
| 5,370,636 A | 12/1994 | Von Witzleben | |
| 5,370,640 A | 12/1994 | Kolff | |
| 5,375,589 A | 12/1994 | Bhatta | |
| 5,380,306 A | 1/1995 | Brinon | |
| 5,380,758 A | 1/1995 | Stamler et al. | |
| 5,391,150 A | 2/1995 | Richmond | |
| 5,402,826 A | 4/1995 | Molnar et al. | |
| 5,405,331 A | 4/1995 | Behnke et al. | |
| 5,405,333 A | 4/1995 | Richmond | |
| 5,405,919 A | 4/1995 | Keefer et al. | |
| 5,407,807 A | 4/1995 | Markus | |
| 5,409,012 A | 4/1995 | Sahatjian | |
| 5,411,499 A | 5/1995 | Dudar et al. | |
| 5,417,673 A | 5/1995 | Gordon | |
| 5,425,465 A | 6/1995 | Healy | |
| 5,428,070 A | 6/1995 | Cooke et al. | |
| 5,433,330 A | 7/1995 | Yatsko et al. | |
| 5,433,705 A | 7/1995 | Giebel et al. | |
| 5,439,451 A | 8/1995 | Collinson et al. | |
| 5,441,487 A * | 8/1995 | Vedder | F16L 15/006 604/167.03 |
| 5,445,623 A | 8/1995 | Richmond | |
| 5,456,668 A | 10/1995 | Ogle, II | |
| 5,456,675 A | 10/1995 | Wolbring et al. | |
| 5,464,399 A | 11/1995 | Boettger | |
| 5,470,307 A | 11/1995 | Lindall | |
| 5,470,327 A | 11/1995 | Helgren et al. | |
| 5,471,706 A | 12/1995 | Wallock et al. | |
| 5,474,536 A | 12/1995 | Bonaldo | |
| 5,480,393 A | 1/1996 | Bommarito | |
| 5,485,827 A | 1/1996 | Zapol et al. | |
| 5,492,147 A | 2/1996 | Challender et al. | |
| 5,496,288 A | 3/1996 | Sweeney | |
| 5,501,426 A | 3/1996 | Atkinson et al. | |
| 5,507,733 A | 4/1996 | Larkin et al. | |
| 5,507,744 A | 4/1996 | Tay et al. | |
| 5,514,177 A | 5/1996 | Kurz et al. | |
| 5,518,026 A | 5/1996 | Benjey | |
| 5,520,665 A | 5/1996 | Fleetwood | |
| 5,520,666 A | 5/1996 | Choudhury et al. | |
| 5,525,357 A | 6/1996 | Keefer et al. | |
| 5,531,695 A | 7/1996 | Swisher | |
| 5,533,708 A | 7/1996 | Atkinson et al. | |
| 5,533,983 A | 7/1996 | Haining | |
| 5,535,785 A | 7/1996 | Werge et al. | |

(56)                References Cited

U.S. PATENT DOCUMENTS

| | | | |
|---|---|---|---|
| 5,536,241 A | 7/1996 | Zapol | |
| 5,536,258 A | 7/1996 | Folden | |
| 5,540,661 A | 7/1996 | Tomisaka et al. | |
| 5,545,614 A | 8/1996 | Stamler et al. | |
| 5,549,566 A | 8/1996 | Elias et al. | |
| 5,549,651 A | 8/1996 | Lynn | |
| 5,552,115 A | 9/1996 | Malchesky | |
| 5,552,118 A | 9/1996 | Mayer | |
| 5,554,127 A | 9/1996 | Crouther et al. | |
| 5,554,135 A | 9/1996 | Menyhay | |
| 5,555,908 A | 9/1996 | Edwards et al. | |
| 5,569,235 A | 10/1996 | Ross et al. | |
| 5,573,516 A | 11/1996 | Tyner | |
| 5,575,769 A | 11/1996 | Vaillancourt | |
| 5,578,059 A | 11/1996 | Patzer | |
| 5,580,530 A | 12/1996 | Kowatsch et al. | |
| 5,584,819 A | 12/1996 | Kopfer | |
| 5,591,137 A | 1/1997 | Stevens | |
| 5,591,143 A | 1/1997 | Trombley, III et al. | |
| 5,597,536 A | 1/1997 | Mayer | |
| 5,599,352 A | 2/1997 | Dinh et al. | |
| 5,605,696 A | 2/1997 | Eury et al. | |
| 5,607,072 A | 3/1997 | Rigney et al. | |
| 5,613,615 A | 3/1997 | Zeyfang et al. | |
| 5,616,130 A | 4/1997 | Mayer | |
| 5,620,088 A | 4/1997 | Martin et al. | |
| 5,620,427 A * | 4/1997 | Werschmidt ....... A61M 39/1011 137/516.13 | |
| 5,624,402 A * | 4/1997 | Imbert ................ A61M 5/3134 604/533 | |
| 5,628,733 A | 5/1997 | Zinreich et al. | |
| RE35,539 E | 6/1997 | Bonaldo | |
| 5,645,538 A | 7/1997 | Richmond | |
| 5,665,077 A | 9/1997 | Resen et al. | |
| 5,674,206 A | 10/1997 | Allton et al. | |
| 5,676,346 A | 10/1997 | Leinsing | |
| 5,685,835 A | 11/1997 | Brugger | |
| 5,685,866 A | 11/1997 | Lopez | |
| 5,685,868 A | 11/1997 | Lundquist | |
| 5,688,253 A | 11/1997 | Lundquist | |
| 5,694,978 A | 12/1997 | Heilmann et al. | |
| 5,699,821 A | 12/1997 | Paradis | |
| 5,700,248 A | 12/1997 | Lopez | |
| 5,702,017 A | 12/1997 | Goncalves | |
| 5,716,339 A | 2/1998 | Tanaka et al. | |
| 5,722,537 A | 3/1998 | Sigler | |
| 5,735,826 A | 4/1998 | Richmond | |
| 5,738,144 A | 4/1998 | Rogers | |
| 5,743,892 A | 4/1998 | Loh et al. | |
| 5,749,861 A | 5/1998 | Guala et al. | |
| 5,763,409 A | 6/1998 | Bayol et al. | |
| 5,770,645 A | 6/1998 | Stamler et al. | |
| 5,776,116 A | 7/1998 | Lopez | |
| 5,782,808 A | 7/1998 | Folden | |
| 5,782,816 A | 7/1998 | Werschmidt et al. | |
| 5,785,693 A | 7/1998 | Haining | |
| 5,792,120 A | 8/1998 | Menyhay | |
| 5,797,887 A | 8/1998 | Rosen et al. | |
| 5,806,831 A | 9/1998 | Paradis | |
| 5,810,792 A | 9/1998 | Fangrow, Jr. et al. | |
| 5,814,024 A | 9/1998 | Thompson et al. | |
| 5,814,666 A | 9/1998 | Green et al. | |
| 5,820,601 A | 10/1998 | Mayer | |
| 5,820,604 A | 10/1998 | Fox et al. | |
| 5,827,244 A | 10/1998 | Boettger | |
| 5,839,715 A | 11/1998 | Leinsing | |
| 5,848,994 A | 12/1998 | Richmond | |
| 5,902,631 A | 5/1999 | Wang et al. | |
| 5,941,857 A | 8/1999 | Nguyen et al. | |
| 5,947,296 A | 9/1999 | Castora | |
| 5,947,954 A | 9/1999 | Bonaldo | |
| 5,951,519 A | 9/1999 | Utterberg | |
| 5,954,957 A | 9/1999 | Chin-Loy et al. | |
| 5,971,972 A | 10/1999 | Rosenbaum | |
| D416,086 S | 11/1999 | Parris et al. | |
| 5,989,229 A | 11/1999 | Chiappetta | |
| 5,994,444 A | 11/1999 | Trescony | |
| 5,996,779 A | 12/1999 | Klardie et al. | |
| 6,029,946 A | 2/2000 | Doyle | |
| 6,036,171 A | 3/2000 | Weinheimer et al. | |
| 6,041,805 A | 3/2000 | Gydesen et al. | |
| 6,045,539 A | 4/2000 | Menyhay | |
| 6,045,623 A | 4/2000 | Cannon | |
| 6,050,978 A | 4/2000 | Orr et al. | |
| 6,059,107 A | 5/2000 | Nosted et al. | |
| 6,063,062 A | 5/2000 | Paradis | |
| 6,068,011 A | 5/2000 | Paradis | |
| 6,068,475 A | 5/2000 | Stoyka, Jr. et al. | |
| 6,068,617 A | 5/2000 | Richmond | |
| 6,071,413 A | 6/2000 | Dyke | |
| 6,079,432 A | 6/2000 | Paradis | |
| 6,087,479 A | 7/2000 | Stamler et al. | |
| 6,093,743 A | 7/2000 | Lai et al. | |
| 6,095,356 A | 8/2000 | Rits | |
| 6,099,519 A | 8/2000 | Olsen et al. | |
| 6,105,812 A | 8/2000 | Riordan | |
| 6,106,502 A | 8/2000 | Richmond | |
| 6,113,068 A | 9/2000 | Ryan | |
| 6,113,572 A | 9/2000 | Gailey et al. | |
| 6,116,468 A | 9/2000 | Nilson | |
| 6,117,114 A | 9/2000 | Paradis | |
| 6,126,640 A | 10/2000 | Tucker | |
| 6,142,446 A | 11/2000 | Leinsing | |
| 6,143,318 A | 11/2000 | Gilchrist et al. | |
| 6,146,363 A | 11/2000 | Giebel et al. | |
| 6,152,913 A | 11/2000 | Feith et al. | |
| 6,158,614 A | 12/2000 | Haines et al. | |
| 6,162,487 A | 12/2000 | Darouiche | |
| 6,170,522 B1 | 1/2001 | Tanida | |
| 6,171,287 B1 | 1/2001 | Lynn et al. | |
| 6,174,539 B1 | 1/2001 | Stamler et al. | |
| 6,179,141 B1 | 1/2001 | Nakamura | |
| 6,183,450 B1 | 2/2001 | Lois | |
| 6,202,870 B1 | 3/2001 | Pearce | |
| 6,202,901 B1 | 3/2001 | Gerber et al. | |
| 6,206,134 B1 | 3/2001 | Stark et al. | |
| 6,206,860 B1 | 3/2001 | Richmond | |
| 6,207,855 B1 | 3/2001 | Toone et al. | |
| 6,217,564 B1 | 4/2001 | Peters et al. | |
| 6,227,391 B1 | 5/2001 | King | |
| 6,232,406 B1 | 5/2001 | Stoy | |
| 6,232,434 B1 | 5/2001 | Stamler et al. | |
| 6,237,800 B1 | 5/2001 | Barrett et al. | |
| 6,242,393 B1 | 6/2001 | Ishida et al. | |
| 6,245,048 B1 | 6/2001 | Fangrow et al. | |
| 6,245,056 B1 | 6/2001 | Walker et al. | |
| 6,248,380 B1 | 6/2001 | Kocher et al. | |
| 6,250,315 B1 | 6/2001 | Ernster | |
| 6,255,277 B1 | 7/2001 | Stamler et al. | |
| 6,267,754 B1 | 7/2001 | Peters | |
| 6,299,132 B1 | 10/2001 | Weinheimer et al. | |
| 6,315,113 B1 | 11/2001 | Britton et al. | |
| 6,315,761 B1 | 11/2001 | Shcherbina et al. | |
| 6,359,167 B2 | 3/2002 | Toone et al. | |
| 6,359,182 B1 | 3/2002 | Stamler et al. | |
| 6,375,231 B1 | 4/2002 | Picha et al. | |
| 6,379,660 B1 | 4/2002 | Saavedra et al. | |
| 6,379,691 B1 | 4/2002 | Tedeschi et al. | |
| 6,394,983 B1 | 5/2002 | Mayoral et al. | |
| 6,402,207 B1 | 6/2002 | Segal et al. | |
| 6,403,759 B2 | 6/2002 | Stamler et al. | |
| 6,409,716 B1 | 6/2002 | Sahatjian et al. | |
| 6,428,520 B1 | 8/2002 | Lopez | |
| 6,431,219 B1 | 8/2002 | Redler et al. | |
| 6,444,318 B1 | 9/2002 | Guire et al. | |
| 6,468,259 B1 | 10/2002 | Djokic et al. | |
| 6,471,978 B1 | 10/2002 | Stamler et al. | |
| 6,488,951 B2 | 12/2002 | Toone et al. | |
| 6,491,965 B1 | 12/2002 | Berry et al. | |
| 6,499,719 B1 | 12/2002 | Clancy et al. | |
| 6,508,792 B2 | 1/2003 | Szames et al. | |
| 6,508,807 B1 | 1/2003 | Peters | |
| 6,538,116 B2 | 3/2003 | Stamler et al. | |
| 6,541,802 B2 | 4/2003 | Doyle | |

(56)          References Cited

U.S. PATENT DOCUMENTS

| | | | |
|---|---|---|---|
| 6,543,745 | B1 | 4/2003 | Enerson |
| 6,550,493 | B2 | 4/2003 | Williamson et al. |
| 6,555,504 | B1 | 4/2003 | Ayai et al. |
| 6,562,781 | B1 | 5/2003 | Berry et al. |
| 6,581,906 | B2 | 6/2003 | Pott et al. |
| 6,583,311 | B2 | 6/2003 | Toone et al. |
| 6,585,691 | B1 | 7/2003 | Vitello |
| 6,595,964 | B2 | 7/2003 | Finley et al. |
| 6,595,981 | B2 | 7/2003 | Huet |
| 6,605,294 | B2 | 8/2003 | Sawhney |
| 6,605,751 | B1 | 8/2003 | Gibbins et al. |
| 6,609,696 | B2 | 8/2003 | Enerson |
| 6,632,199 | B1 | 10/2003 | Tucker et al. |
| 6,634,498 | B2 | 10/2003 | Kayerod et al. |
| 6,656,217 | B1 | 12/2003 | Herzog, Jr. et al. |
| 6,666,852 | B2 | 12/2003 | Niedospial, Jr. |
| 6,673,891 | B2 | 1/2004 | Stamler et al. |
| 6,679,395 | B1 | 1/2004 | Pfefferkorn et al. |
| 6,679,870 | B1 | 1/2004 | Finch et al. |
| 6,681,803 | B2 | 1/2004 | Taneya et al. |
| 6,685,694 | B2 | 2/2004 | Finch et al. |
| 6,692,468 | B1 | 2/2004 | Waldenburg |
| 6,695,817 | B1 | 2/2004 | Fangrow |
| 6,716,396 | B1 | 4/2004 | Anderson |
| 6,722,705 | B2 | 4/2004 | Korkor |
| 6,725,492 | B2 | 4/2004 | Moore et al. |
| 6,745,998 | B2 | 6/2004 | Doyle |
| 6,786,884 | B1 | 9/2004 | DeCant, Jr. et al. |
| 6,808,510 | B1 | 10/2004 | DiFiore |
| 6,827,766 | B2 | 12/2004 | Carnes et al. |
| 6,840,501 | B2 | 1/2005 | Doyle |
| 6,871,087 | B1 | 3/2005 | Hughes et al. |
| 6,875,205 | B2 | 4/2005 | Leinsing |
| 6,875,840 | B2 | 4/2005 | Stamler et al. |
| 6,880,706 | B2 | 4/2005 | Braconnot et al. |
| 6,887,994 | B2 | 5/2005 | Stamler et al. |
| 6,899,315 | B2 | 5/2005 | Mailville et al. |
| 6,911,025 | B2 | 6/2005 | Miyahar |
| 6,916,051 | B2 | 7/2005 | Fisher |
| 6,929,005 | B2 | 8/2005 | Sullivan et al. |
| 6,943,035 | B1 | 9/2005 | Davies et al. |
| 6,955,669 | B2 | 10/2005 | Curutcharry |
| 6,964,406 | B2 | 11/2005 | Doyle |
| 7,004,934 | B2 | 2/2006 | Vaillancourt |
| 7,015,347 | B2 | 3/2006 | Toone et al. |
| 7,030,238 | B2 | 4/2006 | Stamler et al. |
| 7,037,302 | B2 | 5/2006 | Vaillancourt |
| 7,040,598 | B2 | 5/2006 | Raybuck |
| 7,044,441 | B2 | 5/2006 | Doyle |
| 7,045,585 | B2 | 5/2006 | Berry et al. |
| 7,049,308 | B2 | 5/2006 | Stamler et al. |
| 7,052,711 | B2 | 5/2006 | West et al. |
| 7,056,308 | B2 | 6/2006 | Utterberg |
| 7,067,659 | B2 | 6/2006 | Stamler et al. |
| 7,081,109 | B2 | 7/2006 | Tighe |
| 7,083,605 | B2 | 8/2006 | Miyahara |
| 7,087,709 | B2 | 8/2006 | Stamler et al. |
| 7,097,850 | B2 | 8/2006 | Chappa et al. |
| 7,100,891 | B2 | 9/2006 | Doyle |
| 7,125,396 | B2 | 10/2006 | Leinsing et al. |
| 7,140,592 | B2 | 11/2006 | Phillips |
| 7,147,625 | B2 | 12/2006 | Sarangapani et al. |
| 7,160,272 | B1 | 1/2007 | Eyal et al. |
| 7,182,313 | B2 | 2/2007 | Doyle |
| 7,195,615 | B2 | 3/2007 | Tan |
| 7,198,611 | B2 | 4/2007 | Connell et al. |
| 7,244,249 | B2 | 7/2007 | Leinsing et al. |
| 7,259,250 | B2 | 8/2007 | Stamler et al. |
| 7,279,176 | B1 | 10/2007 | West et al. |
| 7,282,186 | B2 | 10/2007 | Lake, Jr. et al. |
| 7,306,197 | B2 | 12/2007 | Parrino et al. |
| 7,306,198 | B2 | 12/2007 | Doyle |
| 7,306,566 | B2 | 12/2007 | Raybuck |
| 7,309,326 | B2 | 12/2007 | Fangrow, Jr. |
| 7,316,669 | B2 | 1/2008 | Ranalletta |
| 7,347,458 | B2 | 3/2008 | Rome et al. |
| 7,347,853 | B2 | 3/2008 | DiFiore et al. |
| 7,350,764 | B2 | 4/2008 | Raybuck |
| 7,361,164 | B2 | 4/2008 | Simpson et al. |
| 7,417,109 | B2 | 8/2008 | Stamler et al. |
| 7,431,712 | B2 | 10/2008 | Kim |
| 7,442,402 | B2 | 10/2008 | Chudzik et al. |
| 7,452,349 | B2 | 11/2008 | Miyahar |
| 7,485,107 | B2 | 2/2009 | DiFiore et al. |
| 7,491,192 | B2 | 2/2009 | DiFiore |
| 7,497,484 | B2 | 3/2009 | Ziman |
| 7,516,846 | B2 | 4/2009 | Hansen |
| 7,588,563 | B2 | 9/2009 | Guala |
| 7,611,505 | B2 | 11/2009 | Ranalletta et al. |
| 7,614,426 | B2 | 11/2009 | Kitani et al. |
| 7,615,034 | B2 | 11/2009 | DiFiore |
| 7,625,907 | B2 | 12/2009 | Stamler et al. |
| 7,635,344 | B2 | 12/2009 | Tennican et al. |
| D607,325 | S | 1/2010 | Rogers et al. |
| 7,645,274 | B2 | 1/2010 | Whitley |
| 7,651,481 | B2 | 1/2010 | Raybuck |
| 7,666,170 | B2 | 2/2010 | Guala |
| 7,708,714 | B2 | 5/2010 | Connell et al. |
| 7,731,678 | B2 | 6/2010 | Tennican et al. |
| 7,731,679 | B2 | 6/2010 | Tennican et al. |
| 7,749,189 | B2 | 7/2010 | Tennican et al. |
| 7,753,891 | B2 | 7/2010 | Tennican et al. |
| 7,758,530 | B2 | 7/2010 | DiFiore et al. |
| 7,758,566 | B2 | 7/2010 | Simpson et al. |
| 7,762,524 | B2 | 7/2010 | Cawthon et al. |
| 7,763,006 | B2 | 7/2010 | Tennican |
| 7,766,182 | B2 | 8/2010 | Trent et al. |
| 7,766,897 | B2 | 8/2010 | Ramsey et al. |
| 7,776,011 | B2 | 8/2010 | Tennican et al. |
| 7,780,794 | B2 | 8/2010 | Rogers et al. |
| 7,785,616 | B2 | 8/2010 | Stamler et al. |
| 7,794,675 | B2 | 9/2010 | Lynn |
| 7,799,010 | B2 | 9/2010 | Tennican |
| 7,803,139 | B2 | 9/2010 | Fangrow, Jr. |
| 7,803,140 | B2 | 9/2010 | Fangrow, Jr. |
| 7,815,614 | B2 | 10/2010 | Fangrow, Jr. |
| 7,857,793 | B2 | 12/2010 | Raulerson et al. |
| 7,922,701 | B2 | 4/2011 | Buchman |
| 7,922,711 | B2 | 4/2011 | Ranalletta et al. |
| 7,928,079 | B2 | 4/2011 | Hrabie et al. |
| 7,938,795 | B2 | 5/2011 | DiFiore et al. |
| 7,956,062 | B2 | 6/2011 | Stamler et al. |
| 7,959,026 | B2 | 6/2011 | Bertani |
| 7,963,565 | B2 | 6/2011 | Suter |
| 7,972,137 | B2 | 7/2011 | Rosen |
| 7,972,322 | B2 | 7/2011 | Tennican |
| 7,981,090 | B2 | 7/2011 | Plishka et al. |
| 7,985,302 | B2 | 7/2011 | Rogers et al. |
| 7,993,309 | B2 | 8/2011 | Schweikert |
| 7,998,134 | B2 | 8/2011 | Fangrow et al. |
| 8,034,454 | B2 | 10/2011 | Terry |
| 8,065,773 | B2 | 11/2011 | Vaillancourt et al. |
| 8,066,670 | B2 | 11/2011 | Cluff et al. |
| 8,069,523 | B2 | 12/2011 | Vaillancourt et al. |
| 8,113,837 | B2 | 2/2012 | Zegarelli |
| 8,146,757 | B2 | 4/2012 | Abreu et al. |
| 8,162,899 | B2 | 4/2012 | Tennican |
| 8,167,847 | B2 | 5/2012 | Anderson et al. |
| 8,172,825 | B2 | 5/2012 | Solomon et al. |
| 8,177,761 | B2 | 5/2012 | Howlett et al. |
| 8,177,772 | B2 | 5/2012 | Christensen et al. |
| 8,197,749 | B2 | 6/2012 | Howlett et al. |
| 8,206,514 | B2 | 6/2012 | Rogers et al. |
| 8,231,587 | B2 | 7/2012 | Solomon et al. |
| 8,231,602 | B2 | 7/2012 | Anderson et al. |
| 8,252,247 | B2 | 8/2012 | Ferlic |
| 8,262,628 | B2 | 9/2012 | Fangrow, Jr. |
| 8,262,643 | B2 | 9/2012 | Tennican |
| 8,273,303 | B2 | 9/2012 | Ferlic et al. |
| 8,281,824 | B2 | 10/2012 | Molema et al. |
| 8,328,767 | B2 | 12/2012 | Solomon et al. |
| 8,336,152 | B2 | 12/2012 | Kerr et al. |
| 8,343,112 | B2 | 1/2013 | Solomon et al. |
| 8,361,408 | B2 | 1/2013 | Lynn |

(56) References Cited

U.S. PATENT DOCUMENTS

| | | | |
|---|---|---|---|
| 8,372,045 B2 | 2/2013 | Needle et al. | |
| 8,377,040 B2 | 2/2013 | Burkholz et al. | |
| 8,414,547 B2 | 4/2013 | DiFiore et al. | |
| 8,419,713 B1 | 4/2013 | Solomon et al. | |
| 8,454,579 B2 | 6/2013 | Fangrow, Jr. | |
| 8,480,968 B2 | 7/2013 | Lynn | |
| 8,491,546 B2 | 7/2013 | Hoang et al. | |
| 8,500,717 B2 | 8/2013 | Becker | |
| 8,506,527 B2 | 8/2013 | Carlyon | |
| 8,506,538 B2 | 8/2013 | Chelak | |
| 8,523,798 B2 | 9/2013 | DiFiore | |
| 8,523,830 B2 | 9/2013 | Solomon et al. | |
| 8,523,831 B2 | 9/2013 | Solomon et al. | |
| 8,533,887 B2 | 9/2013 | Hirst | |
| 8,545,479 B2 | 10/2013 | Kitani et al. | |
| 8,568,371 B2 | 10/2013 | Siopes et al. | |
| 8,622,995 B2 | 1/2014 | Ziebol et al. | |
| 8,622,996 B2 | 1/2014 | Ziebol et al. | |
| 8,641,681 B2 | 2/2014 | Solomon et al. | |
| 8,641,684 B2 | 2/2014 | Utterberg et al. | |
| 8,647,308 B2 | 2/2014 | Solomon et al. | |
| 8,647,326 B2 | 2/2014 | Solomon et al. | |
| 8,651,271 B1 | 2/2014 | Shen | |
| 8,671,496 B2 | 3/2014 | Kerr et al. | |
| 8,740,864 B2 | 6/2014 | Hoang et al. | |
| 8,777,504 B2 | 7/2014 | Shaw et al. | |
| 8,791,073 B2 | 7/2014 | West et al. | |
| 8,845,593 B2 | 9/2014 | Anderson et al. | |
| 8,877,231 B2 | 11/2014 | Rosen | |
| 8,910,919 B2 | 12/2014 | Bonnal et al. | |
| 8,920,404 B2 | 12/2014 | DiFiore et al. | |
| 8,968,268 B2 | 3/2015 | Anderson et al. | |
| 8,981,139 B2 | 3/2015 | Schoenfisch et al. | |
| 8,999,073 B2 | 4/2015 | Rogers et al. | |
| 9,022,984 B2 | 5/2015 | Ziebol et al. | |
| 9,072,296 B2 | 7/2015 | Mills et al. | |
| 9,072,868 B2 | 7/2015 | Ziebol et al. | |
| 9,078,992 B2 | 7/2015 | Ziebol et al. | |
| 9,089,680 B2 | 7/2015 | Ueda et al. | |
| 9,095,500 B2 | 8/2015 | Brandenburger et al. | |
| 9,095,667 B2 | 8/2015 | Von Schuckmann | |
| 9,101,685 B2 | 8/2015 | Li et al. | |
| 9,101,750 B2 | 8/2015 | Solomon et al. | |
| 9,114,915 B2 | 8/2015 | Solomon et al. | |
| 9,125,600 B2 | 9/2015 | Steube et al. | |
| 9,149,624 B2 | 10/2015 | Lewis | |
| 9,180,252 B2 | 11/2015 | Gelblum et al. | |
| 9,192,449 B2 | 11/2015 | Kerr et al. | |
| 9,205,248 B2 | 12/2015 | Wu et al. | |
| 9,216,440 B2 | 12/2015 | Ma et al. | |
| 9,233,208 B2 | 1/2016 | Tekeste | |
| 9,242,084 B2 | 1/2016 | Solomon et al. | |
| 9,248,093 B2 | 2/2016 | Kelley, III et al. | |
| 9,248,229 B2 | 2/2016 | Devouassoux et al. | |
| 9,259,284 B2 | 2/2016 | Rogers et al. | |
| 9,259,535 B2 | 2/2016 | Anderson et al. | |
| 9,283,367 B2 | 3/2016 | Hoang et al. | |
| 9,283,368 B2 | 3/2016 | Hoang et al. | |
| 9,283,369 B2 | 3/2016 | Ma et al. | |
| 9,289,588 B2 * | 3/2016 | Chen | A61M 39/10 |
| 9,296,525 B2 | 3/2016 | Murphy et al. | |
| 9,302,049 B2 | 4/2016 | Tekeste | |
| 9,320,858 B2 | 4/2016 | Grimm et al. | |
| 9,320,859 B2 | 4/2016 | Grimm et al. | |
| 9,320,860 B2 * | 4/2016 | Grimm | A61M 39/26 |
| 9,352,080 B2 | 5/2016 | Goodall et al. | |
| 9,352,140 B2 | 5/2016 | Kerr et al. | |
| 9,352,141 B2 | 5/2016 | Wong | |
| 9,352,142 B2 | 5/2016 | Ziebol et al. | |
| 9,381,339 B2 | 7/2016 | Wu et al. | |
| 9,399,125 B2 * | 7/2016 | Burkholz | A61M 39/162 |
| 9,408,971 B2 | 8/2016 | Carlyon | |
| 9,527,660 B2 | 12/2016 | Tennican | |
| 9,592,375 B2 | 3/2017 | Tennican | |
| 9,700,676 B2 | 7/2017 | Anderson et al. | |
| 9,700,677 B2 | 7/2017 | Anderson et al. | |
| 9,700,710 B2 | 7/2017 | Anderson et al. | |
| 9,707,348 B2 | 7/2017 | Anderson et al. | |
| 9,707,349 B2 | 7/2017 | Anderson et al. | |
| 9,707,350 B2 | 7/2017 | Anderson et al. | |
| 9,809,355 B2 | 11/2017 | Solomon et al. | |
| 9,849,276 B2 | 12/2017 | Ziebol et al. | |
| 9,867,975 B2 | 1/2018 | Gardner et al. | |
| 9,907,617 B2 | 3/2018 | Rogers | |
| 9,933,094 B2 | 4/2018 | Fangrow | |
| 9,999,471 B2 | 6/2018 | Rogers et al. | |
| 10,016,587 B2 | 7/2018 | Gardner et al. | |
| 10,046,156 B2 | 8/2018 | Gardner et al. | |
| 10,159,829 B2 | 12/2018 | Ziebol et al. | |
| 10,166,381 B2 | 1/2019 | Gardner et al. | |
| 10,195,000 B2 | 2/2019 | Rogers et al. | |
| 10,201,692 B2 | 2/2019 | Chang | |
| 10,328,207 B2 | 6/2019 | Anderson et al. | |
| 10,524,982 B2 | 1/2020 | Fangrow | |
| 10,525,250 B1 | 1/2020 | Ziebol et al. | |
| 10,695,550 B2 | 6/2020 | Gardner et al. | |
| 10,744,316 B2 | 8/2020 | Fangrow | |
| 10,806,919 B2 | 10/2020 | Gardner et al. | |
| 10,821,278 B2 | 11/2020 | Gardner et al. | |
| 11,160,932 B2 | 11/2021 | Anderson et al. | |
| 11,229,746 B2 | 1/2022 | Anderson et al. | |
| 11,351,353 B2 | 6/2022 | Ziebol et al. | |
| 11,389,634 B2 | 7/2022 | Ziebol et al. | |
| 11,400,195 B2 | 8/2022 | Ziebol et al. | |
| 11,433,215 B2 | 9/2022 | Ziebol et al. | |
| 11,497,904 B2 | 11/2022 | Fangrow et al. | |
| 11,517,732 B2 | 12/2022 | Ziebol et al. | |
| 11,517,733 B2 | 12/2022 | Fangrow | |
| 11,534,595 B2 | 12/2022 | Ziebol et al. | |
| 11,541,220 B2 | 1/2023 | Ziebol et al. | |
| 11,541,221 B2 * | 1/2023 | Ziebol | A61M 1/285 |
| 11,559,467 B2 | 1/2023 | Fangrow | |
| 11,684,720 B2 | 6/2023 | Anderson et al. | |
| 11,826,539 B2 | 11/2023 | Ziebol et al. | |
| 11,944,776 B2 | 4/2024 | Ziebol et al. | |
| 11,998,715 B2 | 6/2024 | Gardner | |
| 12,042,640 B2 | 7/2024 | Anderson et al. | |
| 12,076,521 B2 | 9/2024 | Gardner et al. | |
| 12,109,365 B2 | 10/2024 | Ziebol | |
| 12,186,520 B2 | 1/2025 | Ziebol et al. | |
| 12,201,760 B2 | 1/2025 | Ziebol et al. | |
| 12,485,263 B2 | 12/2025 | Ziebol et al. | |
| 12,485,264 B2 | 12/2025 | Gardner | |
| 12,539,409 B2 | 2/2026 | Fangrow | |
| 2002/0077693 A1 | 6/2002 | Barclay et al. | |
| 2002/0082586 A1 | 6/2002 | Finley et al. | |
| 2002/0082682 A1 | 6/2002 | Barclay et al. | |
| 2002/0098278 A1 | 7/2002 | Bates et al. | |
| 2003/0039697 A1 | 2/2003 | Zhao et al. | |
| 2003/0062376 A1 | 4/2003 | Sears et al. | |
| 2003/0072783 A1 | 4/2003 | Stamler et al. | |
| 2003/0078242 A1 | 4/2003 | Raad et al. | |
| 2003/0153865 A1 | 8/2003 | Connell et al. | |
| 2003/0199835 A1 | 10/2003 | Leinsing et al. | |
| 2003/0208165 A1 | 11/2003 | Christensen et al. | |
| 2004/0034042 A1 | 2/2004 | Tsuji et al. | |
| 2004/0034329 A1 | 2/2004 | Mankus et al. | |
| 2004/0037836 A1 | 2/2004 | Stamler et al. | |
| 2004/0048542 A1 | 3/2004 | Thomaschefsky et al. | |
| 2004/0052689 A1 | 3/2004 | Yao | |
| 2004/0052831 A1 | 3/2004 | Modak et al. | |
| 2004/0073176 A1 | 4/2004 | Utterberg | |
| 2004/0156908 A1 | 8/2004 | Polaschegg et al. | |
| 2004/0210201 A1 | 10/2004 | Farnan | |
| 2004/0215148 A1 * | 10/2004 | Hwang | A61M 5/3134 |
| | | | 215/200 |
| 2004/0247640 A1 | 12/2004 | Zhao et al. | |
| 2004/0249337 A1 | 12/2004 | DiFiore | |
| 2004/0249338 A1 | 12/2004 | DeCant, Jr. et al. | |
| 2004/0258560 A1 | 12/2004 | Lake, Jr. et al. | |
| 2005/0008763 A1 | 1/2005 | Schachter | |
| 2005/0013836 A1 | 1/2005 | Raad | |
| 2005/0015075 A1 | 1/2005 | Wright et al. | |
| 2005/0065479 A1 | 3/2005 | Schiller et al. | |

(56) References Cited

U.S. PATENT DOCUMENTS

| | | |
|---|---|---|
| 2005/0098527 A1 | 5/2005 | Yates et al. |
| 2005/0124942 A1 | 6/2005 | Richmond |
| 2005/0124970 A1 | 6/2005 | Kunin et al. |
| 2005/0147524 A1 | 7/2005 | Bousquet |
| 2005/0147525 A1 | 7/2005 | Bousquet |
| 2005/0148930 A1 | 7/2005 | Hseih et al. |
| 2005/0152891 A1 | 7/2005 | Toone et al. |
| 2005/0171493 A1 | 8/2005 | Nicholls |
| 2005/0197634 A1 | 9/2005 | Raad et al. |
| 2005/0214185 A1 | 9/2005 | Castaneda |
| 2005/0220882 A1 | 10/2005 | Pritchard et al. |
| 2005/0228362 A1 | 10/2005 | Vaillancourt |
| 2005/0228482 A1 | 10/2005 | Herzog et al. |
| 2005/0256461 A1 | 11/2005 | DiFiore et al. |
| 2005/0265958 A1 | 12/2005 | West et al. |
| 2005/0267421 A1 | 12/2005 | Wing |
| 2005/0271711 A1 | 12/2005 | Lynch et al. |
| 2005/0288551 A1 | 12/2005 | Callister et al. |
| 2006/0004316 A1 | 1/2006 | DiFiore et al. |
| 2006/0024372 A1 | 2/2006 | Utterberg et al. |
| 2006/0030827 A1 | 2/2006 | Raulerson et al. |
| 2006/0058734 A1* | 3/2006 | Phillips ................. A61M 39/26 |
| | | 604/93.01 |
| 2006/0096348 A1 | 5/2006 | DiFiore |
| 2006/0118122 A1 | 6/2006 | Martens et al. |
| 2006/0129109 A1 | 6/2006 | Shaw et al. |
| 2006/0142730 A1 | 6/2006 | Proulx et al. |
| 2006/0149191 A1 | 7/2006 | DiFiore |
| 2006/0161115 A1 | 7/2006 | Fangrow |
| 2006/0195117 A1 | 8/2006 | Rucker et al. |
| 2006/0202146 A1 | 9/2006 | Doyle |
| 2006/0206178 A1 | 9/2006 | Kim |
| 2006/0253084 A1 | 11/2006 | Nordgren |
| 2006/0261076 A1 | 11/2006 | Anderson |
| 2007/0003603 A1 | 1/2007 | Karandikar et al. |
| 2007/0088292 A1 | 4/2007 | Fangrow |
| 2007/0088293 A1 | 4/2007 | Fangrow |
| 2007/0088294 A1 | 4/2007 | Fangrow |
| 2007/0106205 A1 | 5/2007 | Connell et al. |
| 2007/0112333 A1 | 5/2007 | Hoang et al. |
| 2007/0154621 A1 | 7/2007 | Raad |
| 2007/0156118 A1 | 7/2007 | Ramsey et al. |
| 2007/0167910 A1 | 7/2007 | Tennican et al. |
| 2007/0176117 A1 | 8/2007 | Redmond et al. |
| 2007/0179453 A1 | 8/2007 | Lim et al. |
| 2007/0187353 A1 | 8/2007 | Fox et al. |
| 2007/0202177 A1 | 8/2007 | Hoang |
| 2007/0212381 A1 | 9/2007 | DiFiore et al. |
| 2007/0231315 A1 | 10/2007 | Lichte et al. |
| 2007/0248676 A1 | 10/2007 | Stamler et al. |
| 2007/0249996 A1 | 10/2007 | Tennican et al. |
| 2007/0265578 A1 | 11/2007 | Tennican et al. |
| 2007/0282280 A1 | 12/2007 | Tennican |
| 2007/0287989 A1 | 12/2007 | Crawford et al. |
| 2008/0014005 A1 | 1/2008 | Kitabatake |
| 2008/0027399 A1 | 1/2008 | Harding et al. |
| 2008/0027401 A1 | 1/2008 | Ou-Yang |
| 2008/0033371 A1 | 2/2008 | Updegraff et al. |
| 2008/0039803 A1 | 2/2008 | Lynn |
| 2008/0058733 A1 | 3/2008 | Vogt et al. |
| 2008/0093245 A1 | 4/2008 | Periasamy et al. |
| 2008/0095680 A1 | 4/2008 | Steffens et al. |
| 2008/0097315 A1 | 4/2008 | Miner et al. |
| 2008/0097407 A1 | 4/2008 | Plishka |
| 2008/0103485 A1 | 5/2008 | Kruger |
| 2008/0128646 A1 | 6/2008 | Clawson |
| 2008/0132880 A1 | 6/2008 | Buchman |
| 2008/0147047 A1 | 6/2008 | Davis et al. |
| 2008/0161763 A1 | 7/2008 | Harding et al. |
| 2008/0172007 A1 | 7/2008 | Bousquet |
| 2008/0173651 A1 | 7/2008 | Ping |
| 2008/0177250 A1 | 7/2008 | Howlett et al. |
| 2008/0187460 A1 | 8/2008 | Utterberg et al. |
| 2008/0188791 A1 | 8/2008 | DiFiore et al. |
| 2008/0190485 A1 | 8/2008 | Guala |
| 2008/0193211 A1 | 8/2008 | Burton et al. |
| 2008/0235888 A1 | 10/2008 | Vaillancourt et al. |
| 2008/0262465 A1 | 10/2008 | Zinger et al. |
| 2008/0287920 A1 | 11/2008 | Fangrow et al. |
| 2008/0318333 A1 | 12/2008 | Nielsen et al. |
| 2008/0319423 A1 | 12/2008 | Tanghoj et al. |
| 2009/0008393 A1 | 1/2009 | Howlett et al. |
| 2009/0012426 A1 | 1/2009 | Tennican |
| 2009/0024096 A1 | 1/2009 | Hai et al. |
| 2009/0028750 A1 | 1/2009 | Ryan |
| 2009/0062766 A1 | 3/2009 | Howlett et al. |
| 2009/0093757 A1 | 4/2009 | Tennican |
| 2009/0099529 A1 | 4/2009 | Anderson et al. |
| 2009/0126867 A1 | 5/2009 | Decant, Jr. et al. |
| 2009/0137969 A1 | 5/2009 | Colantonio et al. |
| 2009/0149820 A1 | 6/2009 | DiFiore |
| 2009/0163876 A1 | 6/2009 | Chebator et al. |
| 2009/0205151 A1 | 8/2009 | Fisher et al. |
| 2009/0205656 A1 | 8/2009 | Nishibayashi et al. |
| 2009/0247485 A1 | 10/2009 | Ahmed et al. |
| 2009/0247961 A1 | 10/2009 | Carlyon |
| 2009/0259194 A1 | 10/2009 | Pinedjian et al. |
| 2009/0270832 A1 | 10/2009 | Vancaillie et al. |
| 2009/0293882 A1 | 12/2009 | Terry |
| 2010/0004510 A1 | 1/2010 | Kuroshima |
| 2010/0010086 A1 | 1/2010 | Ash et al. |
| 2010/0047123 A1 | 2/2010 | Solomon et al. |
| 2010/0049170 A1 | 2/2010 | Solomon et al. |
| 2010/0050351 A1 | 3/2010 | Colantonio et al. |
| 2010/0059474 A1 | 3/2010 | Brandenburger et al. |
| 2010/0064456 A1 | 3/2010 | Ferlic |
| 2010/0074932 A1 | 3/2010 | Talsma |
| 2010/0106102 A1 | 4/2010 | Ziebol et al. |
| 2010/0106103 A1 | 4/2010 | Ziebol et al. |
| 2010/0137472 A1 | 6/2010 | Ou-Yang |
| 2010/0143427 A1 | 6/2010 | King et al. |
| 2010/0152670 A1 | 6/2010 | Low |
| 2010/0160894 A1 | 6/2010 | Julian et al. |
| 2010/0172794 A1 | 7/2010 | Ferlic et al. |
| 2010/0242993 A1 | 9/2010 | Hoang et al. |
| 2010/0253070 A1 | 10/2010 | Cheon et al. |
| 2010/0280805 A1 | 11/2010 | DiFiore |
| 2010/0292673 A1 | 11/2010 | Korogi et al. |
| 2010/0292674 A1 | 11/2010 | Jepson et al. |
| 2010/0306938 A1 | 12/2010 | Rogers et al. |
| 2010/0318040 A1 | 12/2010 | Kelley, III et al. |
| 2011/0030726 A1 | 2/2011 | Vaillancourt et al. |
| 2011/0044850 A1 | 2/2011 | Solomon et al. |
| 2011/0046564 A1 | 2/2011 | Zhong |
| 2011/0046603 A1 | 2/2011 | Felsovalyi et al. |
| 2011/0054440 A1 | 3/2011 | Lewis |
| 2011/0062703 A1 | 3/2011 | Lopez |
| 2011/0064512 A1 | 3/2011 | Shaw et al. |
| 2011/0071475 A1 | 3/2011 | Horvath et al. |
| 2011/0082431 A1 | 4/2011 | Burgess et al. |
| 2011/0150958 A1 | 6/2011 | Davis et al. |
| 2011/0175347 A1 | 7/2011 | Okiyama |
| 2011/0184338 A1 | 7/2011 | McKay |
| 2011/0184382 A1 | 7/2011 | Cady |
| 2011/0208128 A1* | 8/2011 | Wu ...................... A61M 39/26 |
| | | 604/533 |
| 2011/0217212 A1 | 9/2011 | Solomon et al. |
| 2011/0265825 A1 | 11/2011 | Rogers et al. |
| 2011/0276031 A1 | 11/2011 | Hoang et al. |
| 2011/0277788 A1 | 11/2011 | Rogers et al. |
| 2011/0282302 A1 | 11/2011 | Lopez et al. |
| 2011/0290799 A1 | 12/2011 | Anderson et al. |
| 2011/0311602 A1 | 12/2011 | Mills et al. |
| 2011/0314619 A1 | 12/2011 | Schweikert |
| 2012/0022469 A1 | 1/2012 | Albert et al. |
| 2012/0029483 A1 | 2/2012 | Griffith et al. |
| 2012/0031904 A1 | 2/2012 | Kuhn et al. |
| 2012/0039764 A1 | 2/2012 | Solomon et al. |
| 2012/0083730 A1 | 4/2012 | Rush et al. |
| 2012/0083750 A1 | 4/2012 | Sansoucy |
| 2012/0157965 A1 | 6/2012 | Wotton et al. |
| 2012/0191029 A1 | 7/2012 | Hopf et al. |
| 2012/0195807 A1 | 8/2012 | Ferlic |
| 2012/0216359 A1 | 8/2012 | Rogers et al. |

(56)                     References Cited

U.S. PATENT DOCUMENTS

| | | |
|---|---|---|
| 2012/0216360 A1 | 8/2012 | Rogers et al. |
| 2012/0220955 A1 | 8/2012 | Maseda et al. |
| 2012/0283693 A1 | 11/2012 | Anderson et al. |
| 2012/0283696 A1 | 11/2012 | Cronenberg et al. |
| 2012/0296284 A1 | 11/2012 | Anderson et al. |
| 2012/0302968 A1 | 11/2012 | Tennican |
| 2012/0302970 A1 | 11/2012 | Tennican |
| 2012/0302997 A1 | 11/2012 | Gardner et al. |
| 2012/0315201 A1 | 12/2012 | Ferlic et al. |
| 2013/0006194 A1 | 1/2013 | Anderson et al. |
| 2013/0023828 A1 | 1/2013 | Anderson et al. |
| 2013/0030414 A1 | 1/2013 | Gardner et al. |
| 2013/0035667 A1 | 2/2013 | Anderson et al. |
| 2013/0039953 A1 | 2/2013 | Dudnyk et al. |
| 2013/0053751 A1 | 2/2013 | Holtham |
| 2013/0072908 A1 | 3/2013 | Solomon et al. |
| 2013/0072909 A1 | 3/2013 | Solomon et al. |
| 2013/0085313 A1 | 4/2013 | Fowler et al. |
| 2013/0085474 A1 | 4/2013 | Charles et al. |
| 2013/0098398 A1 | 4/2013 | Kerr et al. |
| 2013/0098938 A1 | 4/2013 | Efthimiadis |
| 2013/0102950 A1 | 4/2013 | DiFiore |
| 2013/0123754 A1 | 5/2013 | Solomon et al. |
| 2013/0134161 A1 | 5/2013 | Fogel et al. |
| 2013/0138085 A1 | 5/2013 | Tennican |
| 2013/0144258 A1 | 6/2013 | Ziebol et al. |
| 2013/0150795 A1 | 6/2013 | Snow |
| 2013/0164189 A1 | 6/2013 | Hadden |
| 2013/0171030 A1 | 7/2013 | Ferlic et al. |
| 2013/0183635 A1 | 7/2013 | Wilhoit |
| 2013/0184679 A1 | 7/2013 | Ziebol et al. |
| 2013/0197485 A1 | 8/2013 | Gardner et al. |
| 2013/0204231 A1 | 8/2013 | Ziebol et al. |
| 2013/0255061 A1 | 10/2013 | Burkholz |
| 2013/0274686 A1 | 10/2013 | Ziebol et al. |
| 2014/0042116 A1 | 2/2014 | Shen et al. |
| 2014/0048079 A1 | 2/2014 | Gardner et al. |
| 2014/0052074 A1 | 2/2014 | Tekeste |
| 2014/0101876 A1 | 4/2014 | Rogers et al. |
| 2014/0155868 A1 | 6/2014 | Nelson et al. |
| 2014/0227144 A1* | 8/2014 | Liu ..................... A61M 39/162 422/300 |
| 2014/0228775 A1 | 8/2014 | Burkholz et al. |
| 2014/0228809 A1 | 8/2014 | Wong |
| 2014/0243797 A1 | 8/2014 | Jensen et al. |
| 2014/0248182 A1 | 9/2014 | Solomon et al. |
| 2014/0261758 A1 | 9/2014 | Wlodarczyk et al. |
| 2014/0336610 A1 | 11/2014 | Michel et al. |
| 2014/0339812 A1 | 11/2014 | Carney et al. |
| 2014/0339813 A1* | 11/2014 | Cederschiold ........ A61J 1/2096 29/525.02 |
| 2014/0366914 A1 | 12/2014 | Kerr et al. |
| 2015/0018774 A1 | 1/2015 | Anderson et al. |
| 2015/0086441 A1 | 3/2015 | She et al. |
| 2015/0141934 A1 | 5/2015 | Gardner et al. |
| 2015/0148287 A1 | 5/2015 | Woo et al. |
| 2015/0157799 A1 | 6/2015 | Chen et al. |
| 2015/0157800 A1 | 6/2015 | Chen et al. |
| 2015/0165127 A1 | 6/2015 | Haefele et al. |
| 2015/0217106 A1 | 8/2015 | Banik et al. |
| 2015/0231380 A1 | 8/2015 | Hoang et al. |
| 2015/0237854 A1 | 8/2015 | Mills et al. |
| 2015/0238703 A1 | 8/2015 | Glocker |
| 2015/0258324 A1 | 9/2015 | Chida et al. |
| 2015/0273199 A1 | 10/2015 | Adams et al. |
| 2015/0297455 A1 | 10/2015 | Sanders et al. |
| 2015/0297881 A1 | 10/2015 | Sanders et al. |
| 2015/0298893 A1 | 10/2015 | Welp |
| 2015/0306367 A1 | 10/2015 | DiFiore |
| 2015/0306369 A1 | 10/2015 | Burkholz et al. |
| 2015/0314119 A1 | 11/2015 | Anderson et al. |
| 2015/0320926 A1 | 11/2015 | Fitzpatrick et al. |
| 2015/0320992 A1 | 11/2015 | Bonnet et al. |
| 2015/0343174 A1 | 12/2015 | Ziebol et al. |
| 2015/0374968 A1 | 12/2015 | Solomon et al. |
| 2016/0001056 A1 | 1/2016 | Nelson et al. |
| 2016/0001058 A1 | 1/2016 | Ziebol et al. |
| 2016/0015863 A1 | 1/2016 | Gupta et al. |
| 2016/0015931 A1 | 1/2016 | Ryan et al. |
| 2016/0015959 A1 | 1/2016 | Solomon et al. |
| 2016/0045629 A1 | 2/2016 | Gardner et al. |
| 2016/0067365 A1 | 3/2016 | Ma et al. |
| 2016/0067471 A1 | 3/2016 | Ingram et al. |
| 2016/0088995 A1 | 3/2016 | Ueda et al. |
| 2016/0089530 A1 | 3/2016 | Sathe |
| 2016/0101223 A1 | 4/2016 | Kelley, III et al. |
| 2016/0101276 A1 | 4/2016 | Tekeste |
| 2016/0106969 A1 | 4/2016 | Neftel |
| 2016/0121097 A1 | 5/2016 | Steele |
| 2016/0144118 A1 | 5/2016 | Solomon et al. |
| 2016/0158520 A1 | 6/2016 | Ma et al. |
| 2016/0158521 A1 | 6/2016 | Hoang et al. |
| 2016/0158522 A1 | 6/2016 | Hoang et al. |
| 2016/0184527 A1 | 6/2016 | Tekeste |
| 2016/0213912 A1 | 7/2016 | Daneluzzi |
| 2016/0220790 A1 | 8/2016 | Borowicz |
| 2016/0250420 A1 | 9/2016 | Maritan et al. |
| 2016/0354596 A1* | 12/2016 | DiFiore ................. A61M 39/20 |
| 2017/0020911 A1 | 1/2017 | Berry et al. |
| 2017/0042636 A1 | 2/2017 | Young |
| 2017/0143447 A1 | 5/2017 | Rogers et al. |
| 2017/0182241 A1* | 6/2017 | DiFiore ............... A61M 39/162 |
| 2017/0203092 A1 | 7/2017 | Ryan et al. |
| 2017/0239443 A1 | 8/2017 | Abitabilo et al. |
| 2018/0028403 A1 | 2/2018 | Fangrow |
| 2018/0085568 A1 | 3/2018 | Drmanovic |
| 2018/0200500 A1 | 7/2018 | Ziebol et al. |
| 2018/0200501 A1 | 7/2018 | Her |
| 2018/0214684 A1 | 8/2018 | Avula et al. |
| 2019/0201681 A1 | 7/2019 | Ziebol et al. |
| 2019/0351211 A1 | 11/2019 | Dombrowski et al. |
| 2020/0069931 A1 | 3/2020 | Fangrow |
| 2020/0085690 A1 | 3/2020 | Fangrow |
| 2020/0121858 A1 | 4/2020 | Anderson et al. |
| 2020/0139037 A1 | 5/2020 | Ziebol et al. |
| 2020/0139101 A1 | 5/2020 | Ziebol et al. |
| 2020/0139102 A1 | 5/2020 | Ziebol et al. |
| 2020/0139103 A1 | 5/2020 | Ziebol et al. |
| 2020/0139104 A1 | 5/2020 | Ziebol et al. |
| 2020/0155794 A1 | 5/2020 | Ziebol et al. |
| 2020/0324102 A1 | 10/2020 | Fangrow |
| 2020/0330741 A1 | 10/2020 | Fangrow |
| 2020/0406020 A1 | 12/2020 | Fangrow |
| 2021/0106805 A1 | 4/2021 | Fangrow |
| 2021/0162194 A1 | 6/2021 | Gardner |
| 2021/0205596 A1 | 7/2021 | Ziebol et al. |
| 2021/0308442 A1 | 10/2021 | Gardner |
| 2022/0226629 A1 | 7/2022 | Ziebel |
| 2022/0288258 A1 | 9/2022 | Gardner |
| 2022/0288376 A1 | 9/2022 | Ziebol |
| 2022/0313977 A1 | 10/2022 | Gugel et al. |
| 2022/0387685 A1 | 12/2022 | Ziebol |
| 2023/0030414 A1 | 2/2023 | Charrier et al. |
| 2023/0105566 A1 | 4/2023 | Fangrow |
| 2023/0121450 A1 | 4/2023 | Ziebol |
| 2023/0288258 A1 | 9/2023 | Gardner |
| 2024/0050729 A1 | 2/2024 | Ziebol |
| 2024/0050730 A1 | 2/2024 | Fangrow |
| 2024/0139489 A1 | 5/2024 | Ziebol |
| 2024/0216667 A1 | 7/2024 | Ziebol |
| 2025/0025663 A1 | 1/2025 | Ziebol |
| 2025/0099686 A1 | 3/2025 | Anderson |
| 2025/0099733 A1 | 3/2025 | Gardner |
| 2025/0121174 A1 | 4/2025 | Ziebol |

FOREIGN PATENT DOCUMENTS

| | | |
|---|---|---|
| CA | 2 148 847 | 12/1995 |
| CA | 2825217 | 3/2007 |
| CA | 2 769 157 | 2/2011 |
| CA | 2 841 832 | 6/2019 |
| CN | 2402327 Y | 10/2000 |
| CN | 2815392 Y | 9/2006 |
| CN | 201150420 Y | 11/2008 |

(56) References Cited

FOREIGN PATENT DOCUMENTS

| | | |
|---|---|---|
| CN | 201519335 U | 7/2010 |
| CN | 102 844 073 A | 12/2012 |
| CN | 103260696 A | 8/2013 |
| CN | 106902402 | 6/2017 |
| CN | 107837428 | 3/2018 |
| DE | 3515665 | 5/1986 |
| DE | 89 06 628 U1 | 9/1989 |
| DE | 43 34 272 | 4/1995 |
| DE | 29617133 | 1/1997 |
| DE | 102007025900 | 12/2008 |
| EP | 0 063 640 | 11/1982 |
| EP | 0 088 341 | 9/1983 |
| EP | 0 108 785 | 5/1984 |
| EP | 0 174 162 | 3/1986 |
| EP | 0 227 219 | 7/1987 |
| EP | 0 237 239 | 9/1987 |
| EP | 0 245 872 | 11/1987 |
| EP | 0 257 485 | 3/1988 |
| EP | 0 639 385 | 2/1995 |
| EP | 0 734 721 | 10/1996 |
| EP | 0 769 265 | 4/1997 |
| EP | 1 061 000 | 10/2000 |
| EP | 1 331 020 | 7/2003 |
| EP | 1 471 011 | 10/2004 |
| EP | 1 442 753 | 2/2007 |
| EP | 1 813 293 | 8/2007 |
| EP | 1 977 714 | 10/2008 |
| EP | 2 444 117 | 4/2012 |
| EP | 2 606 930 | 6/2013 |
| EP | 2 671 604 | 12/2013 |
| EP | 2 731 658 | 5/2014 |
| FR | 2 493 149 A | 5/1982 |
| FR | 2 506 162 | 11/1982 |
| FR | 2 782 910 | 3/2000 |
| GB | 123221 | 2/1919 |
| GB | 2 296 182 | 6/1996 |
| GB | 2 333 097 | 7/1999 |
| GB | 2 387 772 | 10/2003 |
| JP | 57-131462 U | 8/1982 |
| JP | 04-99950 | 2/1992 |
| JP | 05-31180 A | 2/1993 |
| JP | 8-81695 A | 3/1996 |
| JP | 09-216661 A | 8/1997 |
| JP | 2000-157630 A | 6/2000 |
| JP | 2002-210011 | 7/2002 |
| JP | 2002-234567 A | 8/2002 |
| JP | 2002-291906 | 10/2002 |
| JP | 2005-218649 | 8/2005 |
| JP | 2006-182663 A | 7/2006 |
| JP | 2006-223583 A | 8/2006 |
| JP | 2009-006148 | 1/2009 |
| JP | 2009-544450 A | 12/2009 |
| JP | 2011-036691 | 2/2011 |
| JP | 2011-528647 | 11/2011 |
| JP | 2012-020125 | 2/2012 |
| JP | 2013-509274 | 3/2013 |
| JP | 2013-520287 | 6/2013 |
| JP | 2013-530794 A | 8/2013 |
| JP | 2014-117461 | 6/2014 |
| JP | 2014-533593 A | 12/2014 |
| JP | 2015-526195 A | 9/2015 |
| JP | 2015-533614 A | 11/2015 |
| JP | 2016-506856 A | 3/2016 |
| JP | 2017-515553 A | 6/2017 |
| JP | 2020-146096 | 9/2020 |
| JP | 2020-146097 | 9/2020 |
| JP | 2013-99665 | 5/2023 |
| RU | 2 246 321 C1 | 2/2005 |
| WO | WO 83/03975 | 11/1983 |
| WO | WO 85/05040 | 11/1985 |
| WO | WO 92/12746 | 8/1992 |
| WO | WO 93/20806 | 10/1993 |
| WO | WO 95/07691 | 3/1995 |
| WO | WO 96/35416 | 11/1996 |
| WO | WO 96/38136 | 12/1996 |
| WO | WO 1997/19701 | 6/1997 |
| WO | WO 98/12125 | 3/1998 |
| WO | WO 98/48872 | 11/1998 |
| WO | WO 1999/44665 | 9/1999 |
| WO | WO 2001/70199 A1 | 9/2001 |
| WO | WO 2002/05188 | 1/2002 |
| WO | WO 2002/47581 | 6/2002 |
| WO | WO 2002/49544 | 6/2002 |
| WO | WO 2003/015677 | 2/2003 |
| WO | WO 2003/070296 | 8/2003 |
| WO | WO 2004/035129 | 4/2004 |
| WO | WO 2004/112846 | 12/2004 |
| WO | WO 2005/112954 A1 | 12/2005 |
| WO | WO 2005/112974 A2 | 12/2005 |
| WO | WO 2006/007690 | 1/2006 |
| WO | WO 2006/044236 | 4/2006 |
| WO | WO 2006/102756 | 10/2006 |
| WO | WO 2007/008511 | 1/2007 |
| WO | WO 2007/056773 | 5/2007 |
| WO | WO 2007/137056 | 11/2007 |
| WO | WO 2008/014437 | 1/2008 |
| WO | WO 2008/042285 | 4/2008 |
| WO | WO 2008/086631 | 7/2008 |
| WO | WO 2008/089196 | 7/2008 |
| WO | WO 2008/100950 | 8/2008 |
| WO | WO 2008/140807 | 11/2008 |
| WO | WO 2009/002474 | 12/2008 |
| WO | WO 2009/060322 | 5/2009 |
| WO | WO 2009/117135 | 9/2009 |
| WO | WO 2009/123709 | 10/2009 |
| WO | WO 2009/136957 | 11/2009 |
| WO | WO 2009/153224 | 12/2009 |
| WO | WO 2010/002757 | 1/2010 |
| WO | WO 2010/002808 | 1/2010 |
| WO | WO 2010/011616 | 1/2010 |
| WO | WO 2010/034470 | 4/2010 |
| WO | WO 2010/039171 | 4/2010 |
| WO | WO 2010/062589 | 6/2010 |
| WO | WO 2011/012379 | 2/2011 |
| WO | WO 2011/028722 | 3/2011 |
| WO | WO 2011/053924 | 5/2011 |
| WO | WO 2011/106374 | 9/2011 |
| WO | WO 2011/119021 | 9/2011 |
| WO | WO 2012/009456 | 1/2012 |
| WO | WO 2012/118829 | 9/2012 |
| WO | WO 2012/162006 | 11/2012 |
| WO | WO 2013/009998 | 1/2013 |
| WO | WO 2013/023146 | 2/2013 |
| WO | WO 2013/082180 | 6/2013 |
| WO | WO 2013/184716 | 12/2013 |
| WO | WO 2013/192574 | 12/2013 |
| WO | WO 2014/031628 | 2/2014 |
| WO | WO 2014/074419 | 5/2014 |
| WO | WO 2014/074929 | 5/2014 |
| WO | WO 2014/126867 | 8/2014 |
| WO | WO 2014/140949 | 9/2014 |
| WO | WO 14/159346 | 10/2014 |
| WO | WO 2015/074087 | 5/2015 |
| WO | WO 2015/119940 | 8/2015 |
| WO | WO 2015/120336 | 8/2015 |
| WO | WO 2015/164129 | 10/2015 |
| WO | WO 2015/164134 | 10/2015 |
| WO | WO 2015/168677 | 11/2015 |
| WO | WO 2015/174953 | 11/2015 |
| WO | WO 2016/025775 | 2/2016 |
| WO | WO 2016/182822 | 11/2016 |
| WO | WO 2017/015047 | 1/2017 |
| WO | WO 2017/127364 | 7/2017 |
| WO | WO 2017/127365 | 7/2017 |
| WO | WO 2018/009653 | 1/2018 |
| WO | WO 2018/071717 | 4/2018 |
| WO | WO 2018/204206 | 11/2018 |
| WO | WO 2018/237090 | 12/2018 |
| WO | WO 2018/237122 | 12/2018 |
| WO | WO 2019/178560 | 9/2019 |
| WO | WO 2019/246472 | 12/2019 |
| WO | WO 2020/097366 | 5/2020 |
| WO | WO 2020/251947 | 12/2020 |
| WO | WO 2022/125474 | 6/2022 |

(56)                    References Cited

FOREIGN PATENT DOCUMENTS

OTHER PUBLICATIONS

Thread Check Inc., ISO 80369-7 replaces ISO 594-2:1998€, retrieved 2023; ISO 80369-7 published Oct. 2016, https://www.threadcheck.com/isl-80369/technicalinfo#gref (Year: 2016).

Antibiotic Lock Therapy Guideline, Stanford Hospital and Clinics, Pharmacy Department Policies and Procedures, issued Jun. 2011.

Otto, Mosby's Pocket Guide to Infusion Therapy. Elsevier Health Sciences, 2004. pp. 65-66. Accessed at: http://books.google.com/books?id=j8T14HwWdS4C&lpg=PP1&pg=PP1#v=onepage&f=false (Year: 2004).

"Small-bore connectors for liquids and gases in healthcare applications—Part : Connectors forintravascular or hypodermic applications," ISO 80369-7, Corrected version dated Dec. 1, 2016 (50 pages).

Hospira, "You Work in Neverland," Lifeshield Product Brochure in 2 pages, Published 2009.

Baxter Minicap: Photographs of the Baxter Minicap (Sep. 1, 1998) (4 pages).

Baxter, "Peritoneal Dialysis Patient Connectology," Product Descriptions in 1 page, downloaded Jul. 1, 2011.

Beta Cap II Advertisement from Quinton Instrument Co. (Aug. 1981).

Catheter Connections, "Introducing DualCap," Product Brochure in 1 page, Copyright 2011.

Charney, "Baxter Healthcare Interlink™ IV Access System" in 1 page, from Handbook of Modern Hospital Safety. Published Mar. 1999.

Clave® Needlefree Connector, icumedial, human connections, 2 page brochure. 2012, M1-1065 Rev. 04.

Conical Fittings: International Standard, "Conical fittings with 6% (Luer) Taper for Syringes, Needles and certain Other Medical Equipment—Part 2: Lock Fittings", Ref. No. ISO 594-2:1998. International Organization for Standardization (Sep. 1, 1998) 2nd ed. (16 pages).

Devine, redacted version of letter from David A. Divine, Esq. of Lee & Hayes, dated May 16, 2011 (3 pages).

Devine, redacted version of letter from David A. Divine, Esq. of Lee & Hayes, dated May 27, 2011 (3 pages).

Du. Y, et al. Protein adsorption on polyurethane catheters modified with a novel antithrombin-heparin covalent complex, Journal of Biomedical Materials Research Part A, 2006, 216-225.

Holmer, E. et al. The molecular-weight dependence of the rate-enhancing effect of heparin on theinhibition of thrombin, Factor Xa, Factor IXa, Factor XIa, Factor XIIa and kallikrein by antithrombin, Biochem. J. (1981) 193, 395-400.

Hyprotek, "Port Protek," Product Brochure in 1 page, downloaded Sep. 19, 2011 from http://www.hyprotek.com/products.html.

ICU Medical Antimicrobial Microclave, first sold Jan. 21, 2010, p. 1-2.

Klement, P. et al. Chronic performance of polyurethane catheters covalently coated with ATH complex: A rabbit jugular vein model, Biomaterials, (2006), 27, 5107-5117.

Menyhay et al., "Disinfection of Needleless Catheter Connectors and Access Ports with Alcohol MayNot Prevent Microbial Entry: The Promise of a Novel Antiseptic-Barrier Cap" Infection Control Hospital and Epidemiology, vol. 27, No. 1 (Jan. 2006) (5 pages).

V-Link Luer Activated Device, with VitalShield Protective Coating, 2 page brochure, Baxter Dec. 2009.

International Preliminary Report on Patentability, re PCT Application No. PCT/US16/30844, issued Nov. 14, 2017.

International Search Report and Written Opinion, re PCT Application No. PCT/US16/30844, mailed Jul. 20, 2016.

Photographs of the Baxter Minicap (Sep. 1, 1998) (4 pages).

Value Plastics, Inc., "Finger Snap Luer Lock Ring (FSLLR)," drawn by Frank Lombardi, May 29, 2011.

Melaiye, et al., "Silver and its application as an antimicrobial agent," Expert Opinion on Therapeutic Patents, 15:2, pp. 125-130, (Year: 2005).

* cited by examiner

MEDICAL CONNECTORS CONFIGURED TO RECEIVE EMITTERS OF THERAPEUTIC AGENTS

CROSS REFERENCE TO RELATED APPLICATIONS

This patent application is a continuation of U.S. patent application Ser. No. 16/694,564, filed Nov. 25, 2019, which is a continuation of U.S. patent application Ser. No. 15/726, 838, now U.S. Pat. No. 10,524,982, filed Oct. 6, 2017, which is a continuation of International Application No. PCT/US2016/030844, filed May 4, 2016, which claims the benefit of priority to U.S. Provisional Patent Application No. 62/212,473, filed Aug. 31, 2015, and U.S. Provisional Patent Application No. 62/159,130, filed May 8, 2015. All of the foregoing applications are hereby incorporated by reference herein in their entireties.

BACKGROUND

Field

The inventions relate generally to medical connectors and specifically to medical connectors for use in fluid infusion or transfer systems.

Description of the Related Art

Medical connectors are used to attach or interface between or among two or more medical components of patient fluid infusion systems, such as fluid lines or tubes (e.g., catheters), pumps, syringes, IV bags, drip chambers, infusion ports, injection sites, and/or shunts, etc.

Many different types of fluids are used in patient fluid infusion or transfer systems, including hydrating fluids (e.g., saline), nourishing fluids, pain-diminishing medications, antibiotics, antimicrobials, anti-inflammatories, sedatives, anticoagulants, chemotherapy drugs, bodily fluids (e.g., blood in dialysis procedures), and/or other types of medicinal fluids. In health clinics and hospitals, many different types of medicinal fluids need to be purchased, inventoried, stored, and made available to healthcare practitioners, which requires substantial storage space and is expensive, complex, and time-consuming.

In some situations, a fluid line is attached in fluid communication with a patient's vascular system, such as through an injection site into a blood vessel (e.g., an artery or vein). During an initial infusion phase, one or more medicinal fluids are infused through the fluid line into the patient's bloodstream. After the initial infusion phase is complete, the fluid line is sometimes left in place in a standby phase for an extended period until one or more subsequent infusions are performed. While the fluid line is in the standby phase, with the fluid stagnant, the risk of microbial invasion and colonization increases.

To diminish this risk, healthcare practitioners sometimes infuse a small amount of antimicrobial fluid into the end of a fluid line at the beginning of a standby phase to form a microbial block at the entrance of the fluid line. Before the next infusion phase, the antimicrobial fluid is generally removed by aspirating it from the fluid line into a syringe, and then discarding it, in order to avoid infusing the antimicrobial fluid into the patient. This antimicrobial block procedure is usually very effective, but sometimes it is not performed in clinical settings because it requires the purchase, inventory, retrieval, and infusion of an additional medicinal fluid and related disposables, which further adds to the burden of an otherwise onerous fluid supply system in the health clinic or hospital.

In some medical procedures, one or more additives are desired to be added to a particular medical fluid that is flowing through a fluid line for a variety of therapeutic purposes; however, the process for adding such additives requires obtaining and storing bulky liquid containers and utilizing some type of slow liquid-additive infusion procedure.

SUMMARY

In some embodiments, a medical fluid connector is configured to receive an emitter of therapeutic agents to be emitted into a fluid pathway within the connector, the medical fluid connector comprising a proximal female end, an intermediate region, a distal male end, and a fluid pathway extending from the proximal female end, through the intermediate region, to the distal male end. A retaining structure is positioned within the intermediate region. In some embodiments, the retaining structure is configured to securely receive an emitter of one or more therapeutic agents in a position and orientation in which the fluid pathway is configured to convey fluid moving longitudinally through the fluid pathway directly into a proximal region of the emitter, around one or more outside lateral surfaces of the emitter, and toward the distal male end. In some embodiments, the retaining structure is configured to retain the emitter by way of only a friction fit or an interference fit between the retaining structure and the emitter, and not by way of other retaining methods (e.g., adhesive, sonic welding, entrapment between separable housing pieces, coating, molding, heat staking, solvent bonding, chemical bonding, etc.). In some embodiments, any retaining method can be used. In some embodiments, the medical fluid connector is open from end to end in that the connector is configured to allow at least a portion of the fluid to travel freely into and/or from the proximal female end, through the intermediate region, and to and/or out of the distal male end.

In some embodiments, a medical fluid connector comprises a housing with a proximal region and a distal region, with a fluid pathway extending between the proximal and distal regions. The fluid pathway is configured to receive and convey fluid through the housing. In some embodiments, the housing contains an emitter of one or more therapeutic agents that is securely positioned within the housing in a location in which the fluid pathway is configured to pass adjacent to and outside of at least a majority of the external surface area of the emitter. In some embodiments, the fluid pathway is at least partially open and configured to convey fluid freely through the housing about the emitter.

In some embodiments, a method of manufacturing a medical fluid connector is provided. In some embodiments, the method includes one or more of the following steps: (a) providing a housing comprising a proximal female end, an intermediate region, a distal male end, in which a fluid pathway extends from the proximal female end, through the intermediate region, to the distal male end; (b) providing a retaining structure positioned within the intermediate region, the retaining structure comprising a retaining space and a plurality of fluid flow spaces generally surrounding the retaining space; and (c) inserting an emitter of one or more therapeutic agents into the retaining space, such that the emitter is securely retained within the housing and the emitter is configured to remain secured within the connector when fluid moves longitudinally through the fluid pathway directly into a proximal region of the emitter, around one or more outside lateral surfaces of the emitter, and toward the distal male end.

Any of the embodiments described above, or described elsewhere herein, can include one or more of the following features.

In some embodiments, the medical fluid connector comprises an emitter. In some embodiments, the medical fluid connector comprises one or more additional emitters. In some embodiments, the emitter is configured to emit one or more antimicrobial agents into the fluid pathway when fluid passes through the connector. In some embodiments, the emitter is substantially cylindrical, substantially rectangular, substantially spherical, substantially conical, substantially pyramidal, or substantially cubical. In some embodiments, the retaining structure comprises a plurality of longitudinal struts. In some embodiments, the retaining structure comprises a plurality of base portions.

In some embodiments, the proximal female region near the proximal female end comprises a connection structure. In some embodiments, the connection structure comprises a screw thread. In some embodiments, at least a portion of the screw thread is oversized. In some embodiments, the screw thread comprises a disconnection-resistant feature.

In some embodiments, the distal region comprises a distal male protrusion. In some embodiments, the distal male protrusion is oversized.

Some embodiments pertain to a method of providing an antimicrobial block for a standby patient fluid infusion line. In some embodiments, the method comprises attaching a proximal portion of a medical connector to a syringe containing a liquid. In some embodiments, the medical connector comprises an emitter of one or more antimicrobial agents. In some embodiments, the medical connector is configured to securely position the emitter inside of a fluid pathway of the medical connector. In some embodiments, the method comprises attaching a distal portion of the medical connector to a proximal end of a standby fluid line of a patient. In some embodiments, the method comprises infusing fluid from the syringe, through the proximal portion of the medical connector, into contact with at least upper and lateral external surfaces of the emitter, thereby emitting one or more therapeutic agents into the fluid pathway. In some embodiments of the method, the emitter is positioned within an intermediate region of the connector.

Some embodiments pertain to a method of providing an antimicrobial block for a fluid infusion line. In some embodiments, the method comprises providing a connector with an emitter of an antimicrobial agent, the emitter being securely positioned inside of a fluid pathway of the medical connector. In some embodiments, the method comprises instructing a user to attach a proximal portion of the medical connector to a syringe containing a liquid. In some embodiments, the method comprises instructing a user to infuse a fluid from the syringe, through the proximal portion of the medical connector, into contact with at least upper and lateral external surfaces of the emitter to thereby emit one or more therapeutic agents into the fluid pathway.

4

Figure 1:
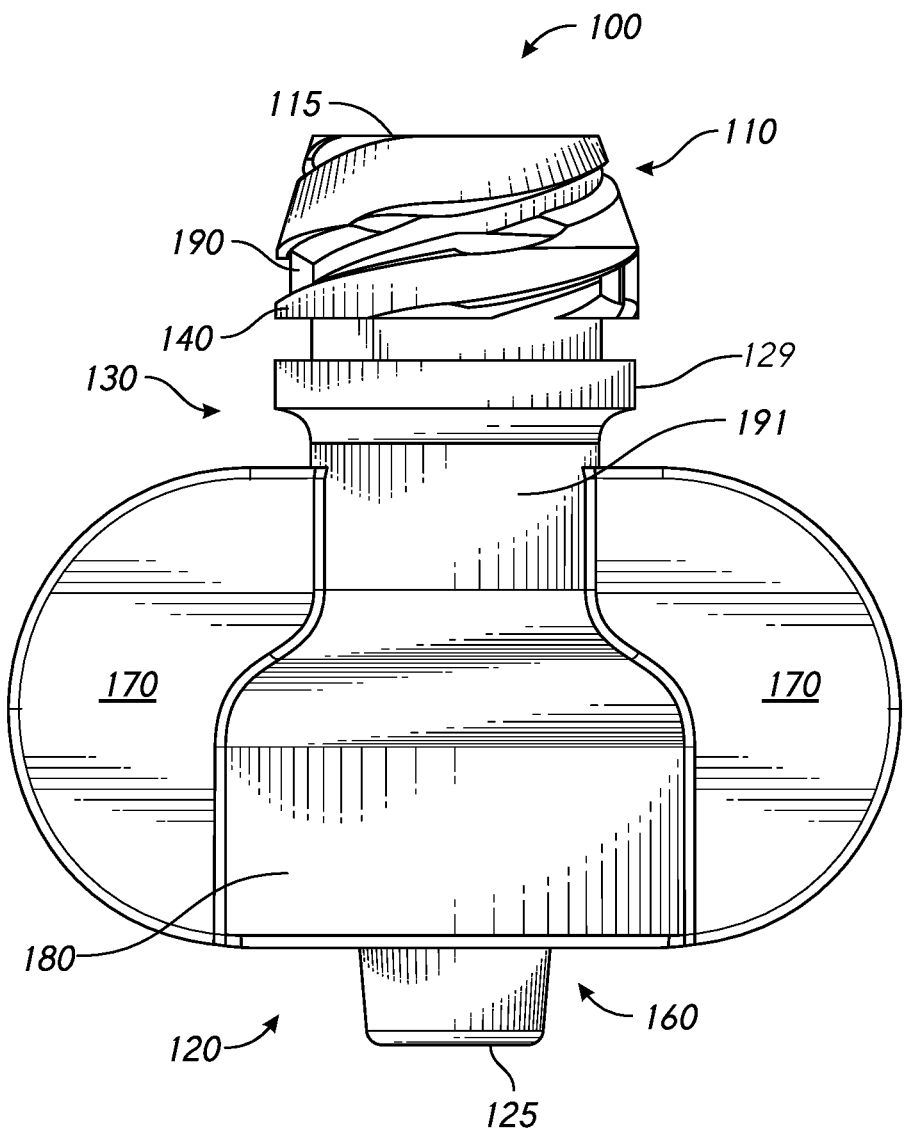
FIG. 1 is a front view of a medical connector that is configured to receive one or more emitters of one or more therapeutic agents.
Figure 2:
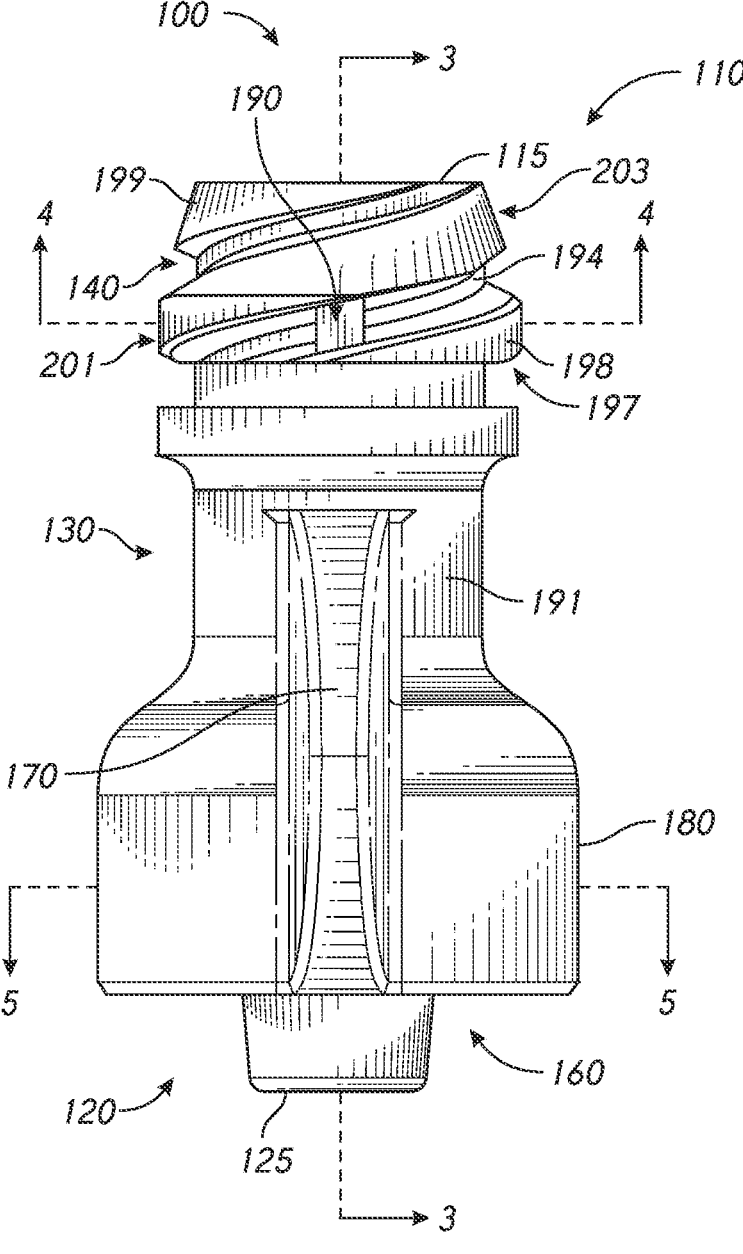
Figure 3A:
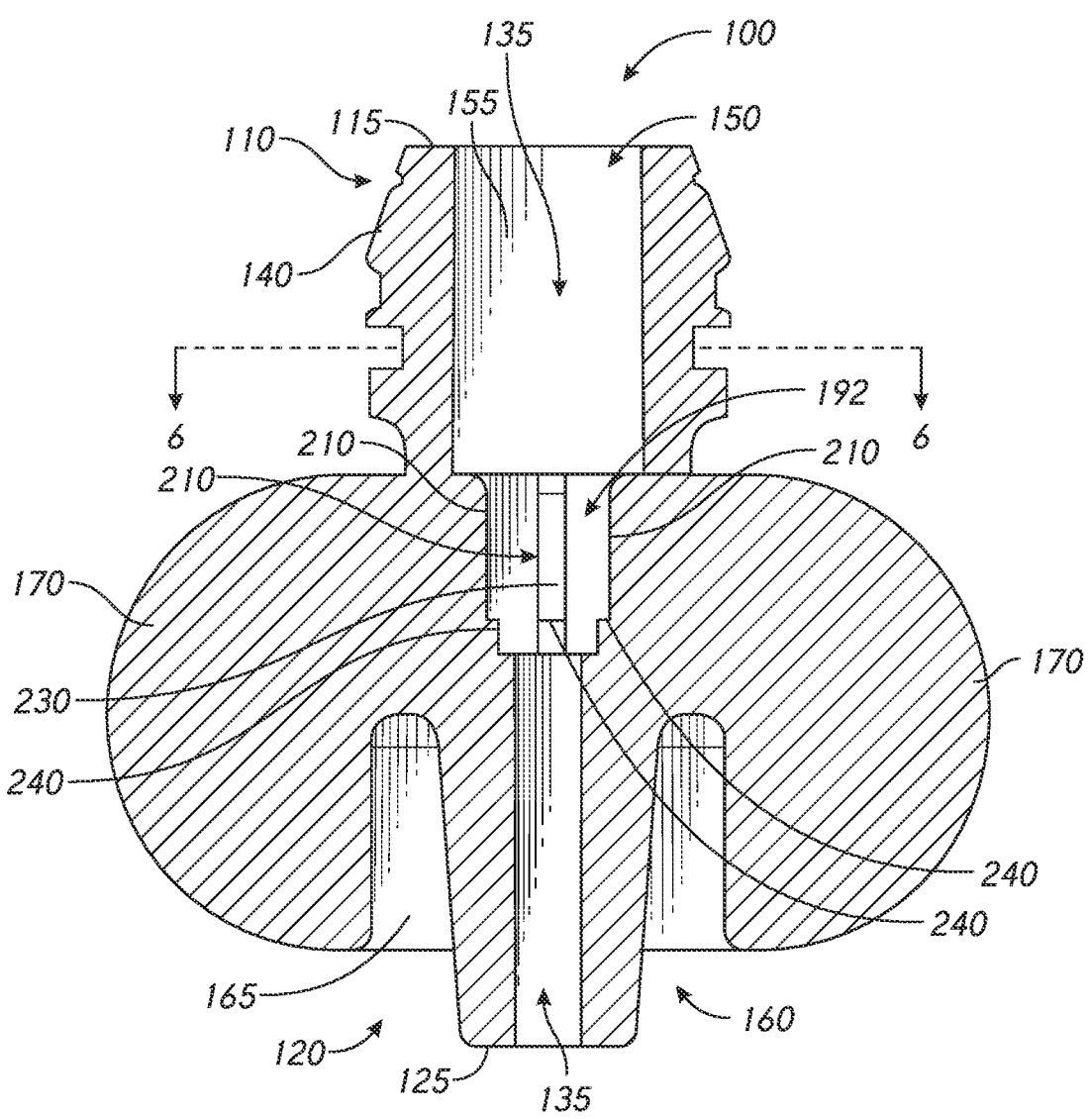
Figure 3B:
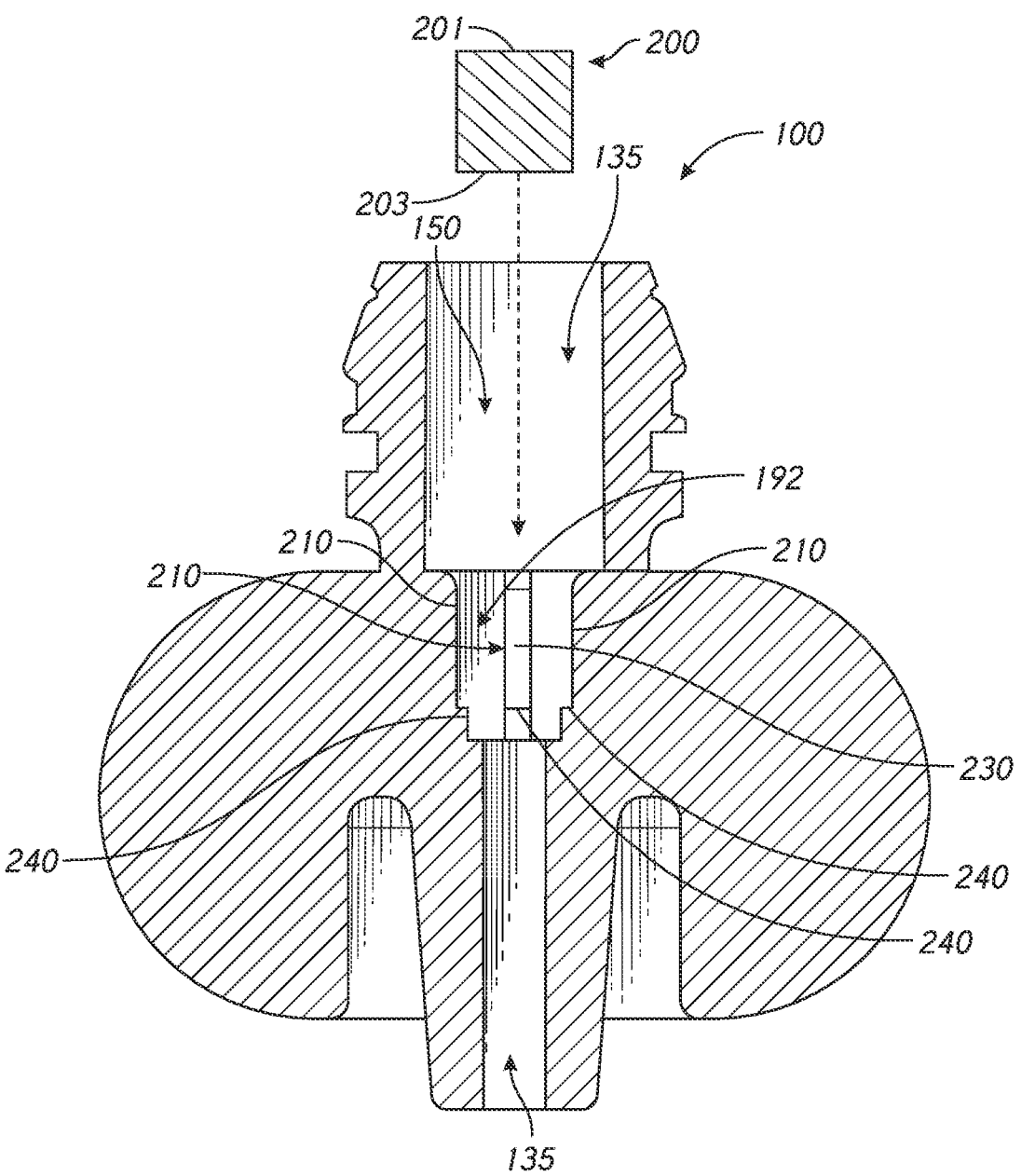
Figure 3C:
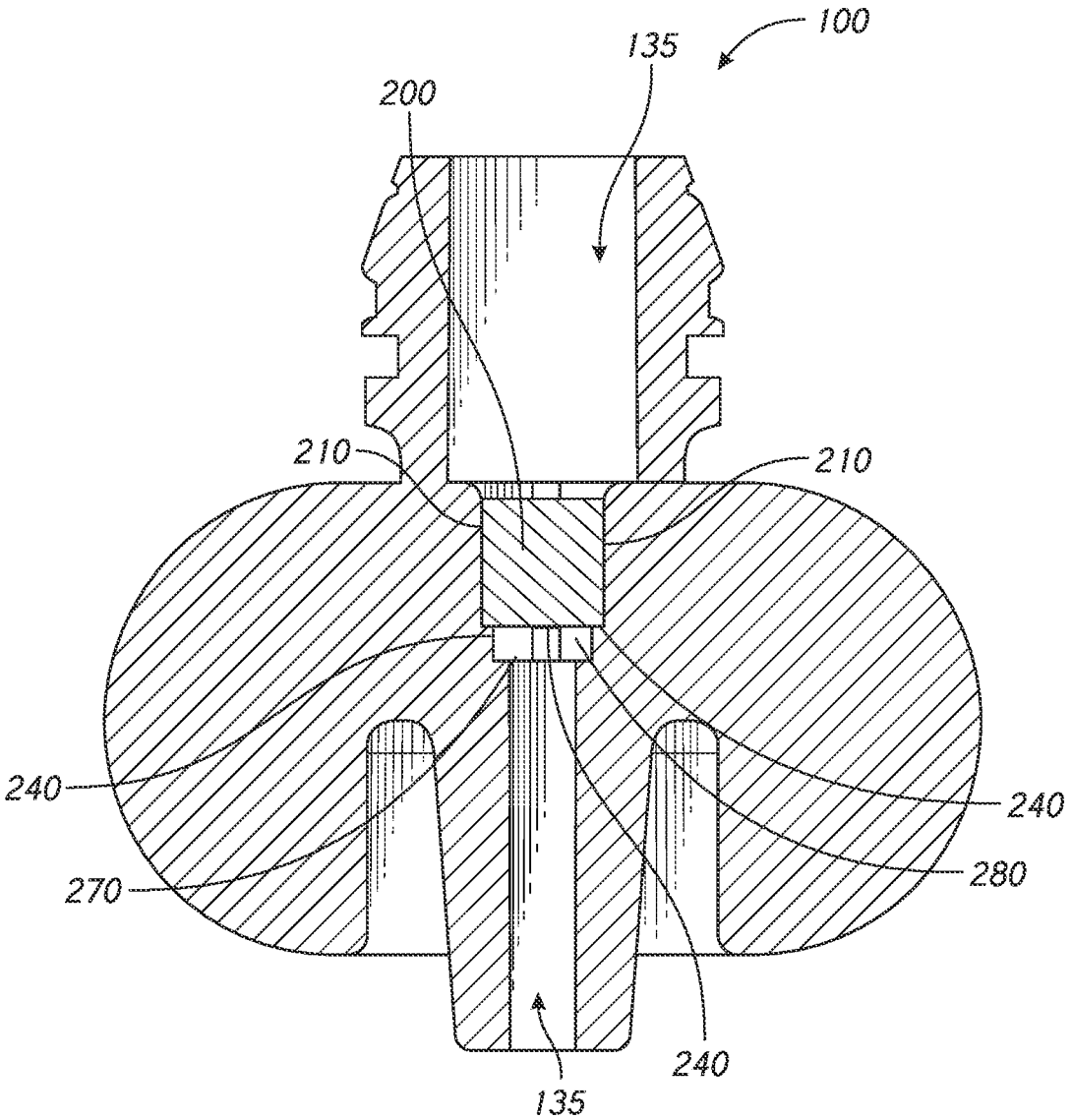
Figure 4:
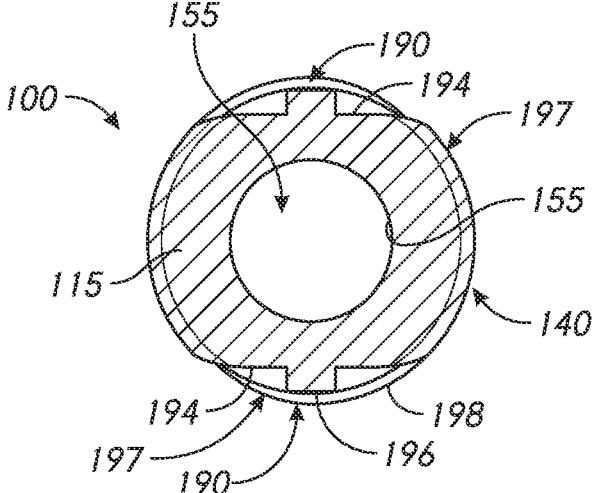
Figure 5:
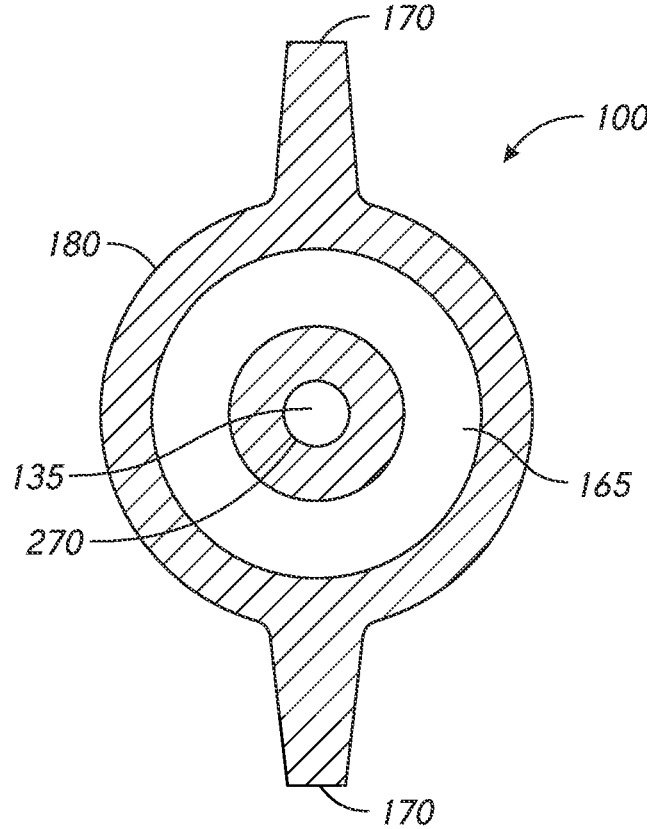
Figure 6A:
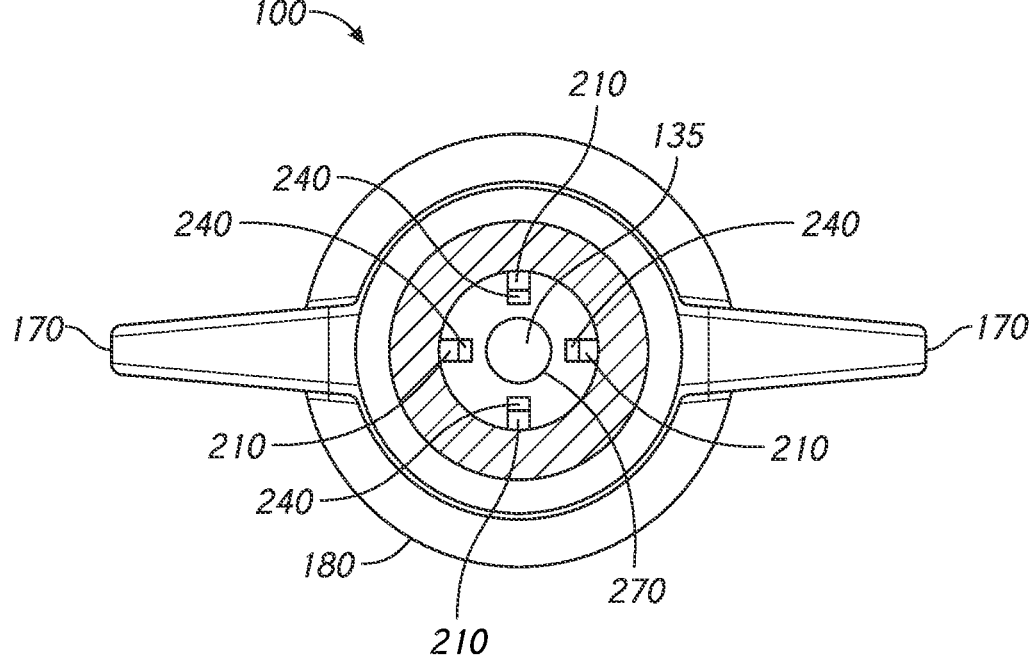
Figure 6B:
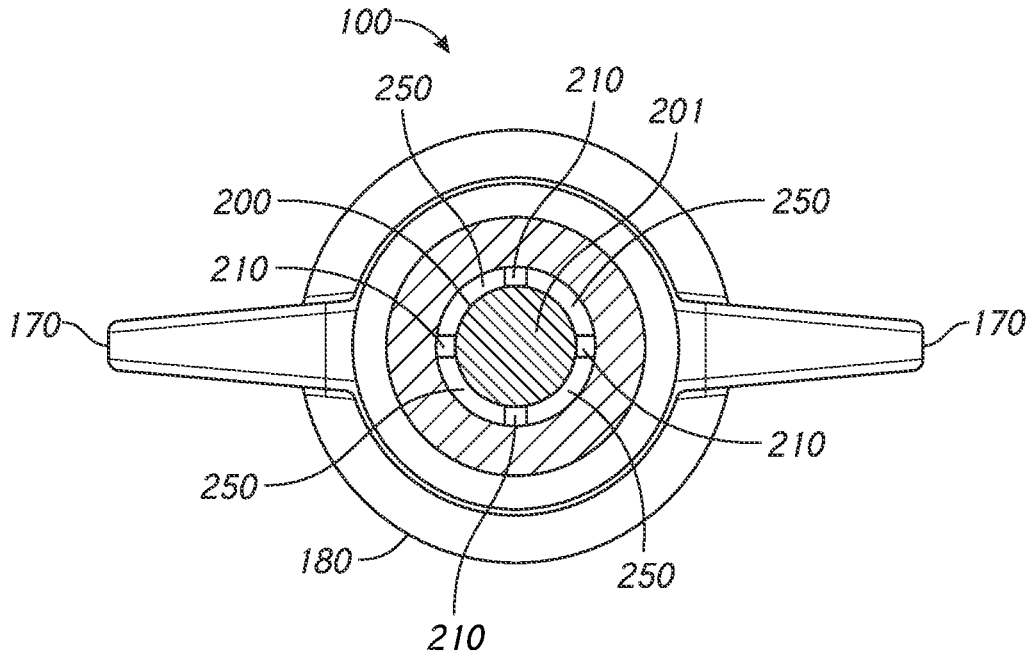
Figure 6C:
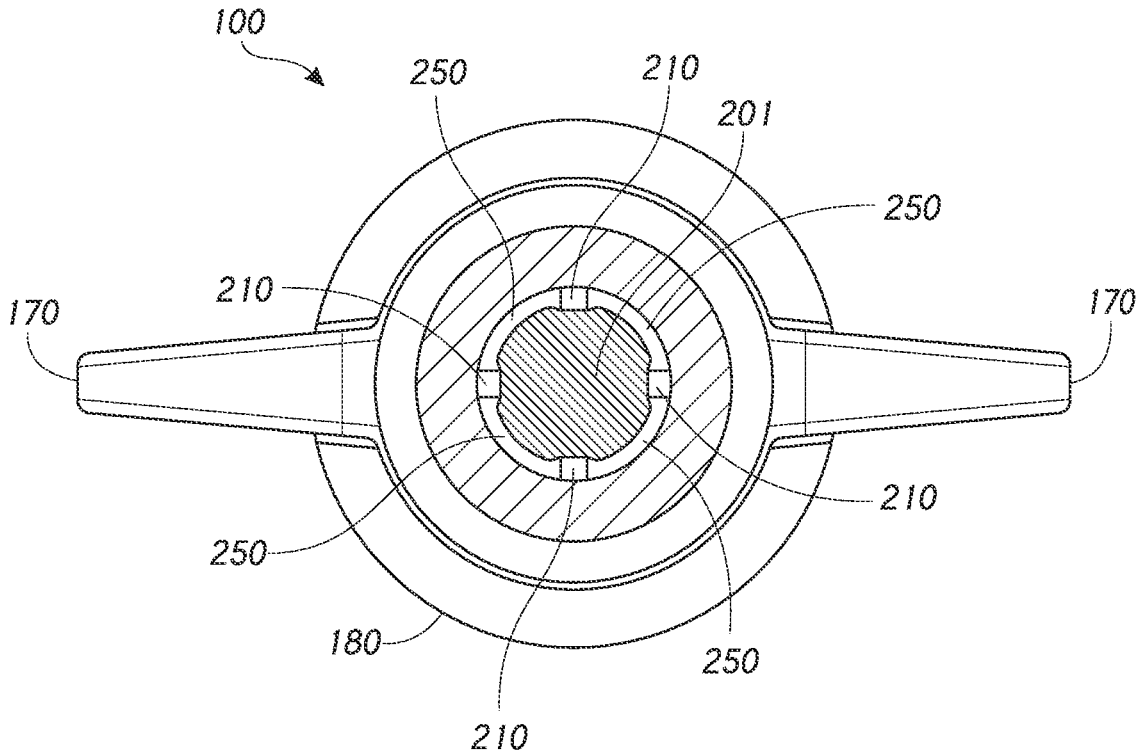
Figures 7A, 7B, 7C:
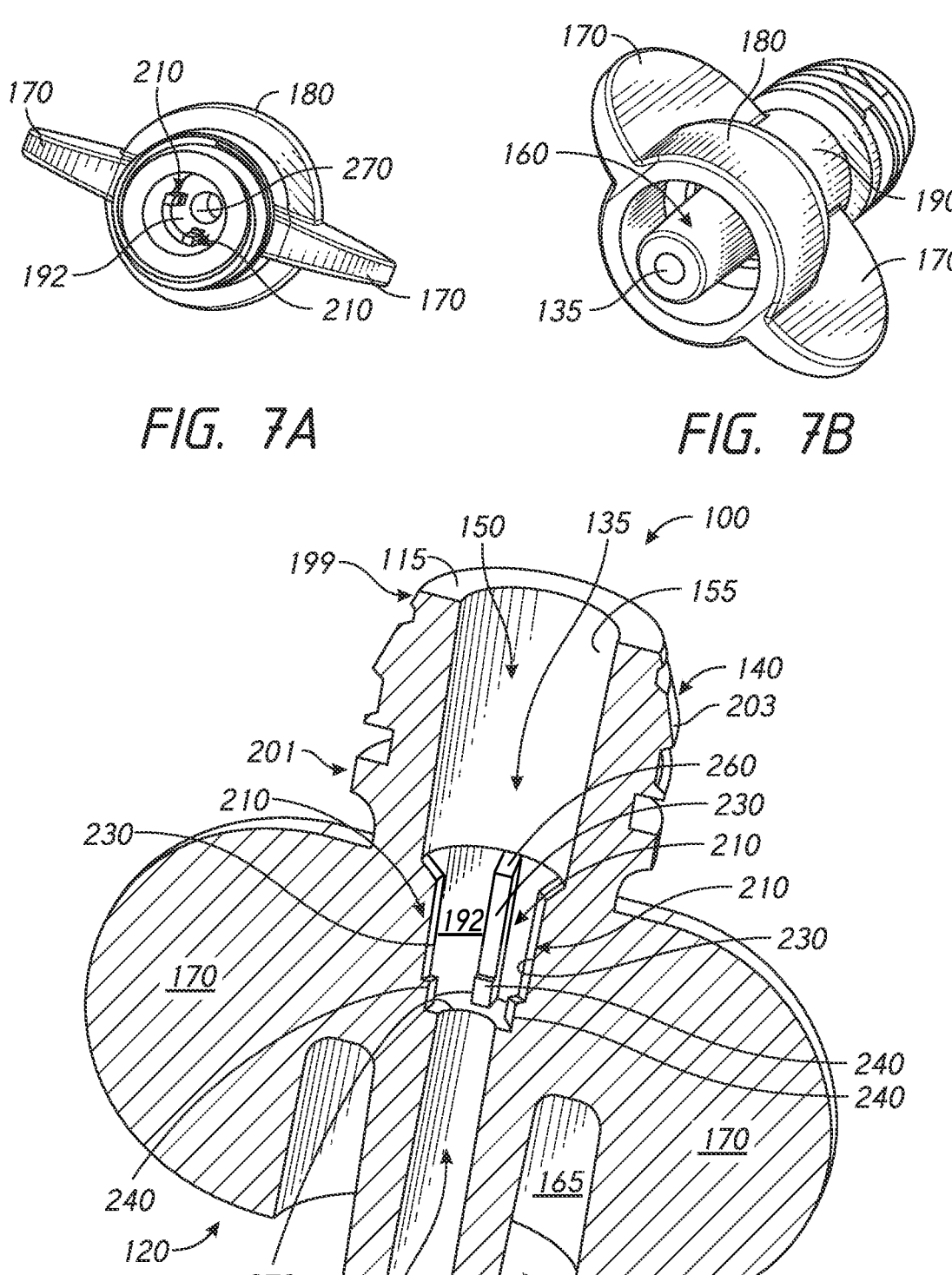
Figure 8:
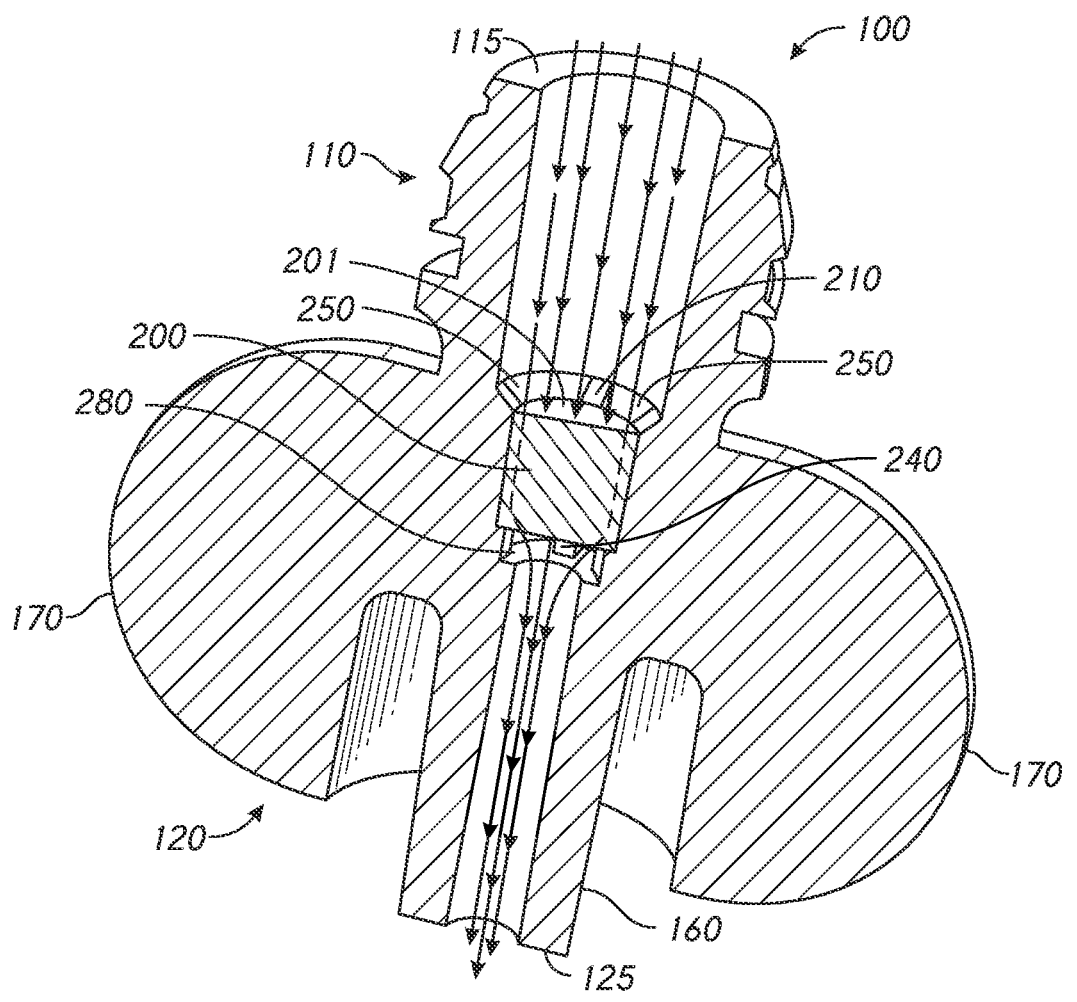
Figure 8A:
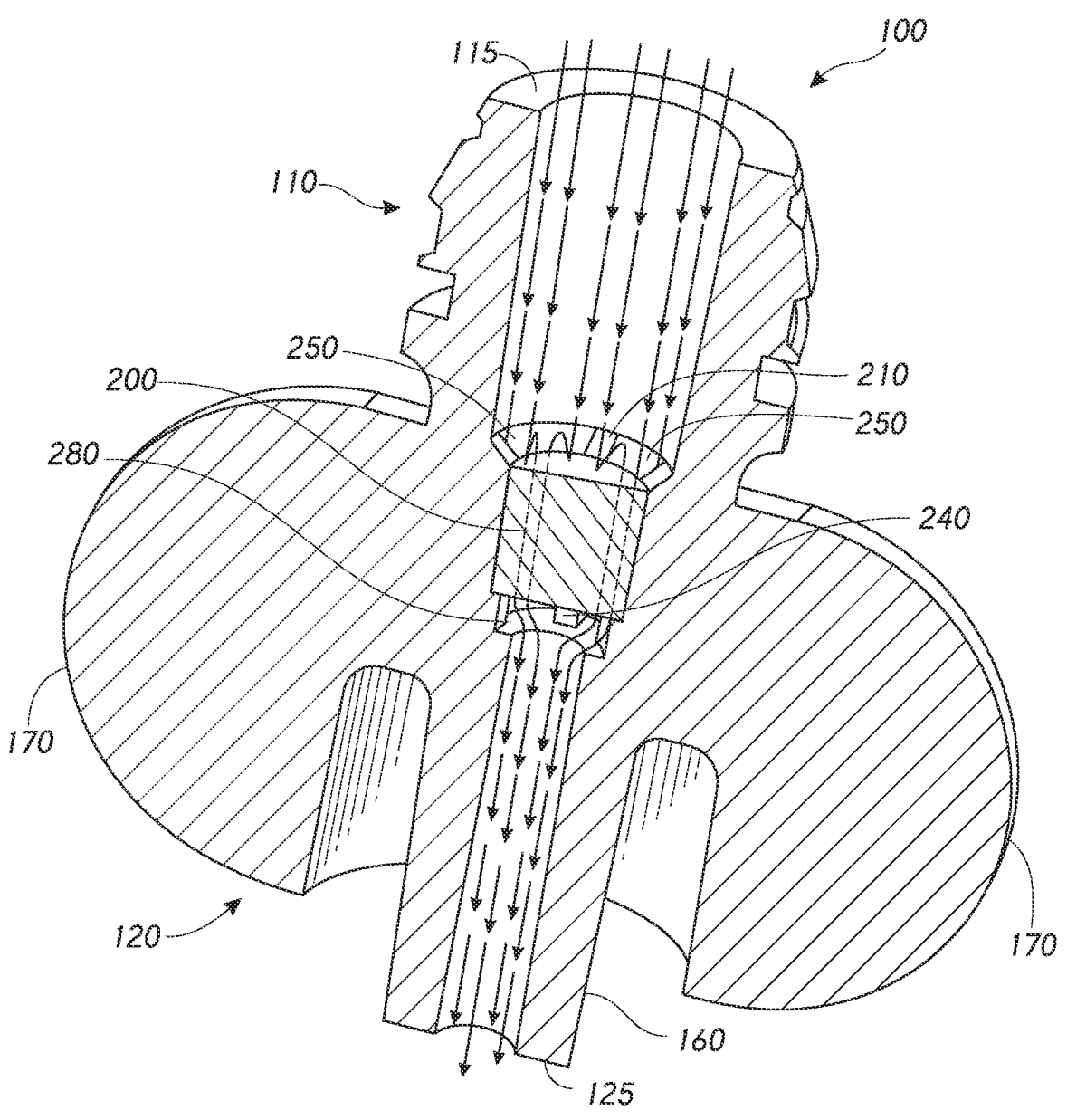

FIG. 2 is a side view of the medical connector of FIG. 1;

FIG. 3A is a front view of the medical connector of FIG. 1 in a vertical cross section along line 3-3 of FIG. 2;

FIG. 3B is the front view of FIG. 3A with an emitter of one or more therapeutic agents being inserted into the fluid pathway;

FIG. 3C is the front view of FIG. 3A with the emitter securely positioned in the fluid pathway;

FIG. 4 is a bottom view of the medical connector of FIG. 1 at a horizontal cross section along line 4-4 of FIG. 2;

FIG. 5 is a top view of the medical connector of FIG. 1 at a horizontal cross section along line 5-5 of FIG. 2;

FIG. 6A is a top view of the medical connector of FIG. 1 with a horizontal cross section along line 6-6 of FIG. 3A;

FIG. 6B is the top view of FIG. 6A with an emitter of one or more therapeutic agents inserted into the fluid pathway;

FIG. 6C is a top view of FIG. 6A with a different type of emitter of one or more therapeutic agents inserted into the fluid pathway (e.g., an emitter with a larger diameter or cross-sectional width than the emitter of FIG. 6B);

FIG. 7A is a top perspective view of the medical connector of FIG. 1;

FIG. 7B is a bottom perspective view of the medical connector of FIG. 1;

FIG. 7C is a front perspective view of the medical connector of FIG. 1 with a vertical cross section along line 4-4 of FIG. 2;

FIG. 8 is the front perspective view of FIG. 7C with an emitter securely positioned in the fluid pathway and fluid flowing through the connector; and FIG. 8A is another front perspective view of FIG. 7C illustrating another example of fluid flow through the connector.

Nothing illustrated in these drawings or described in the associated text is indispensable or essential; rather, any feature, structure, material, component, or step illustrated or described in any embodiment can be used alone or omitted, or can be used with or instead of any feature, structure, material, component, or step illustrated or described in any other embodiment. For example, some embodiments do not include any emitter, but do include one or more other features illustrated or described in this specification. The features are illustrated and described in discrete embodiments merely for convenience of explanation, but not to limit the inventions or to segregate the inventions into isolated collections of features. The proportions and relative sizes of components and features illustrated in the drawings form part of this disclosure, but should only be interpreted to form part of a claim if recited in such claim, either now or in the future.

DETAILED DESCRIPTION

FIGS. 1-7 illustrate an example of a medical connector 100. Different embodiments of medical connectors are described in this specification, some of which include the features illustrated in FIG. 1-7. A medical connector 100 comprises a housing comprising a proximal region 110 with a proximal end 115, a distal region 120 with a distal end 125, and a body 130 extending between the proximal and distal ends 115, 125. The distal region 120 can comprise a male protrusion 160, such as a male luer protrusion. An internal fluid pathway 135 can extend between the proximal and distal regions 110, 120 of the connector 100, such as between the proximal and distal ends 115, 125. In some embodiments, either or both of the proximal or distal regions 110, 120 can include a connection structure 140, such as one or more threads (as shown), clasps, arms, latches, protrusions, and/or recesses, etc., that is configured to help guide, attach, and/or retain the medical connector to another device, such as another medical connector.

As shown in FIGS. 1 and 2, the proximal region 110 can comprise a threaded connection structure 140 configured to rotatably attach and detach from a corresponding threaded connection structure on another device, such as a male end of a syringe (not shown). A thread-stop or collar 129 can be positioned distally from the connection structure 140 to prevent or resist over-extending the threaded connection between the connector 100 and another medical device. As illustrated in FIGS. 3A-C and 4, the proximal region can include a female coupling 150 configured to slidably receive a corresponding male coupling of another device such as a syringe (not shown). In some embodiments, as shown, the female coupling 150 comprises a conduit 155 within the proximal region 110. The conduit 155 can comprise a tapering wall structure that diminishes in diameter or horizontal cross-sectional width from the proximal end 115 toward the distal end 125. In some embodiments, the taper can conform to a standard within the medical industry, such as any version of the ISO 594 standard (which includes a 6% luer taper) or any other applicable standard (e.g., DIN and EN standard 1707:1996 and/or 20594-1:1993). The conduit 155 can be configured to snugly and tightly receive a male coupling of another standard-compliant device with a corresponding taper or other shape, such as a corresponding luer taper, to produce resistance against fluid leakage after the male coupling is inserted fully into the female coupling 150. In some embodiments, as shown, the connector 100 is separate from the syringe; and in some embodiments, the connector 100 is integrated into or bonded to the syringe.

In some embodiments, as illustrated, the connection structure 140 can comprise one or more disconnection-resisting features or structures configured to resist disconnection between the connector 100 and another medical implement (such as a syringe or other connector or other structure). The disconnection-resisting features(s) or structure(s) can have many different forms, such as one or more freely spinning positions or stages after connection is accomplished, one or more increased friction-inducing anti-rotation impediments, and/or one or more disconnection-resisting thread shapes. For example, in a threaded connection structure 140, as shown in FIGS. 1, 2, and 4, a friction-inducing impediment can comprise one or more (e.g., at least two) protrusions 190 positioned between multiple thread turns, the one or more protrusions 190 extending radially outwardly from the inner surface 194 of the threading 197, thereby providing a region of radial space between the radially outermost surface 196 of the protrusion 190 and the radially outermost surface 198 of the threading 197 that is smaller than the radial space between the inner surface 194 of the threading 197 and the outermost surface 198 of the threading 197. In this example of an impediment, as the threading of another device (such as a syringe, not shown) is rotatably attached to the threading 197 of the connection structure 140, the relative rotation of the two devices is slowed down or resisted through increased frictional contact between the impediment and the threading of the other device, thereby requiring greater torque to attach the two devices and/or requiring greater torque to detach the two devices, which diminishes the risk of accidental disconnection. The contact between the impediment and the threading of the other device may cause wedging, compaction, crushing, and/or compression of either or both structures. Many different types of impediments can be used to resist disconnection that are different from those described and/or illustrated.

A disconnection-resisting thread shape can help resist or prevent disconnection between the connector 100 and another medical device, such as a syringe. For example, as illustrated in FIGS. 1, 2, and 7C, a helical threading 197 with multiple thread turns can comprise a thread portion with an oversized region 201, and/or an outwardly flaring or outwardly tapering region 203. In some embodiments, as shown, the outermost diameter of a beginning thread portion 199 can be a first diameter that is a standard size or within a standard range of sizes, such as may be specified in any applicable medical device standard (e.g., any of those mentioned elsewhere in this specification), or slightly smaller than a standard size or range of sizes. As the thread progresses around the proximal region 110 in the distal direction, the outermost diameter of a portion of the thread can flare or taper outwardly to a non-standard second diameter than is larger than the first diameter and larger than the diameter or range of diameters specified in one or more applicable medical device standards. Since the other medical device to which the proximal region 110 of the connector 100 is configured to attach (e.g., a syringe) will typically have a standard diameter of threading, the outward taper or flare of the disconnection-resisting thread shape of the connector 100 can cause the space between the respective threads to decrease, or can cause the attachment region of the other medical device to stretch by a small amount, and/or can cause the threading 197 of the connector 100 to compress by a small amount. One or more of these effects can create opposing radial forces between the threading surface of the other medical device and the threading surface 197 of the connector 100, which can increase the friction between the respective surfaces and thereby resist or prevent rotational movement and decrease the risk of accidental disconnection between the two devices. As shown in this example, the connector 100 can be configured to resist disconnection from a syringe. In some embodiments, the connection structure 140 is configured such that the resistance is sufficiently high that it is not possible under normal conditions of use to disconnect the connector 100 from the other medical device (e.g., disconnection is prevented). Many other different types of disconnection-resisting or disconnection-preventing features can be used instead of or in addition to those illustrated and/or described in this specification, including one or more structures not including thread shapes or impediments, or any type of threads at all.

In some uses, it may be desirable to temporarily attach the distal region 120 of the connector 100 to a standby fluid line that has at its proximal end a resealable needleless female connector, such as a Clave® connector sold by ICU Medical, Inc. or a SmartSite® connector sold by CareFusion Corporation. This type of configuration can allow a healthcare practitioner to infuse fluid from a fluid source (such as a syringe) into the proximal end 115 of connector 100, through the distal end 125 of connector 100, and into the resealable needleless female connector, the fluid line, and ultimately the patient. However, it may be undesirable, in some embodiments, to leave the connector 100 attached to a resealable female connector for a prolonged period, especially when unattended, since the connector 100 may not include a seal at its proximal end in some embodiments (as shown), and may therefore expose the fluid in the fluid line to the outside environment or even allow fluid in the fluid line to flow out of the fluid line. Thus, in some embodiments, there is no connection-securing structure (such as threads) in the distal region 120 of the connector 100 to discourage long-term connection. Rather, the illustrated connector 100, without connection-securing structure, is configured to be rapidly and easily slidably inserted into and/or removed from a corresponding female connector without requiring any additional motion (e.g., twisting, rotating, clasping, etc.) in a non-secured connection. Also, the absence of connection-securing structure in the distal region 120 of the connector obviates the need to use a reverse twisting motion to remove the distal region 120 from the resealable needleless female connector, which would otherwise increase the risk that a threadably secured connection between a syringe and the proximal region 110 of the connector would be inadvertently partially or completely disconnected or backed out, potentially causing a leak.

In some embodiments (not shown), the distal region 120 can comprise any suitable connection structure, such as any connection structure that is illustrated and/or described in connection with the proximal region 110 of medical connector 100 or in connection with any other embodiment. If used, the connection structure can be included in an inner region 165 generally surrounding the male luer protrusion 160. As illustrated, the inner region 165 can be generally surrounded by a shroud or skirt that is configured to pass over and around a corresponding female end of another fluid connector to which the male protrusion 160 of the connector 100 is configured to be attached. As illustrated in FIG. 7C, in some embodiments, the proximal end of the inner region 165 is positioned further in the distal direction than the distal end of the intermediate region 192. In some embodiments, including those in which there is no gripping portion 170 in the distal region 120 of the connector 120 (or no gripping portion 170 at all), the shroud or skirt can be omitted, as with any other feature, structure, material, or step disclosed or illustrated in this specification. When the shroud or skirt is omitted, the male protrusion 160 can be fully exposed along its length from a proximal base region to a distal end region.

The male protrusion 160 can include one or more features to facilitate temporary attachment to a resealable needleless female connector. For example, the male protrusion 160 may not be a standard luer, in that it may have a non-standard size and/or shape (e.g., a size and/or shape that does not conform with one or more features or requirements of one or more medical industry standards, such as the ISO 594 medical luer standard and/or one or more other medical standards). In the illustrated embodiment, the male protrusion 160 has a taper that is about 6%, which comports with one or more medical standards, but the male protrusion 160 is oversized in that it has a larger outer diameter on its distal end than is specified in one or more medical standards. For example, in some embodiments, the distal outer diameter of the male protrusion 160 can be at least about $\frac{1}{1,000}$ of an inch and or at least about $\frac{3}{1,000}$ of an inch larger than a standard distal outer diameter. Many other sizes can be used.

Since most resealable needleless female connectors have proximal openings with standard-size diameters, the oversized, non-standard male protrusion 160 will have a larger diameter at its distal end than the diameter at the distal end of the conduit of the female opening in a standard medical device to which the connector 100 is configured to attach. The larger diameter on the male protrusion 160 can enable it to fit more tightly or snugly at a lesser penetration depth into the female opening than would a male luer protrusion with a standard distal outer diameter. This can help to facilitate a non-secured, temporary attachment of the distal region 120 of the connector 100 to a resealable needleless female connector (not shown). Most, if not all, resealable needleless female connectors include a compressible elastomeric sealing element or other movable sealing element that can be advanced distally within such connector to temporarily open it to fluid flow, such as by inserting the male protrusion 160 into a proximal female opening on such a resealable needleless female connector. The sealing element is configured to rebound to a sealed position by pushing back against an inserted male protrusion. The amount of rebound or push-back force increases as the penetration depth of the inserted male protrusion increases. Since the male protrusion 160 is non-standard, having a larger distal outer diameter, it penetrates less distance into the needleless female connector when fully inserted, and therefore the sealing element exerts less proximally-directed rebound force against it, lowering the risk that the male protrusion 160 will be pushed back in the proximal direction by the sealing element and thereby dislodged from the resealable needleless female connector.

As shown, in some embodiments, the overall longitudinal length of the connector 100 can be relatively short. For example, either or both of the longitudinal length of the portion of the fluid pathway 135 within the threaded region (or the region on which the connection structure 140 is affixed, in some embodiments) and/or the longitudinal length of the portion of the fluid pathway 135 within the male protrusion 160 can be greater than the longitudinal length of the portion of the fluid pathway 135 that extends between the threaded region and the male protrusion 160, as shown in FIG. 3. As illustrated, a base portion 180 of the distal region 120 of the connector 100 can be relatively wide. For example, the external diameter and/or external horizontal cross sectional width of the base portion 180 can be larger than an external neck portion 191 located between the proximal region 110 and the base portion 180. Many different sizes and proportions of the portions of the connector 100 can be used.

The connector 100 can comprise a grasping portion 170, such as one or more tabs (as shown), recesses, protrusions, stripes, bumps, and/or friction-inducing gripping surfaces, etc. In the embodiment illustrated in FIG. 1, the grasping portion 170 enables a user to securely retain the connector 110 during connection and disconnection with another device, such as when another device is twisted, or swayed or rocked back and forth, onto or away from the threaded proximal region 110, or when the threaded proximal region 110 is twisted, or swayed or rocked back and forth, into or out of another device.

The grasping portion 170 can be relatively large in comparison to the size of the overall connector 100. For example, as shown in FIGS. 5 and 6, the horizontal cross-sectional width (e.g., extending between respective lateral edges) of the grasping portion 170 can be larger than the external diameter or horizontal cross-sectional width of the base portion 180, in some embodiments. As illustrated, the longitudinal length (in the proximal-to-distal dimension) of the grasping portion 170 can be larger than the longitudinal length of the connection structure 140 in the proximal region 110 of the connector 100. In some embodiments, as shown, the longitudinal length of the grasping portion 170 can extend over more than half of the overall longitudinal length of the connector 100. The grasping portion 170 can comprise one or more curved lateral edges or sides, as illustrated.

Figure 1A:
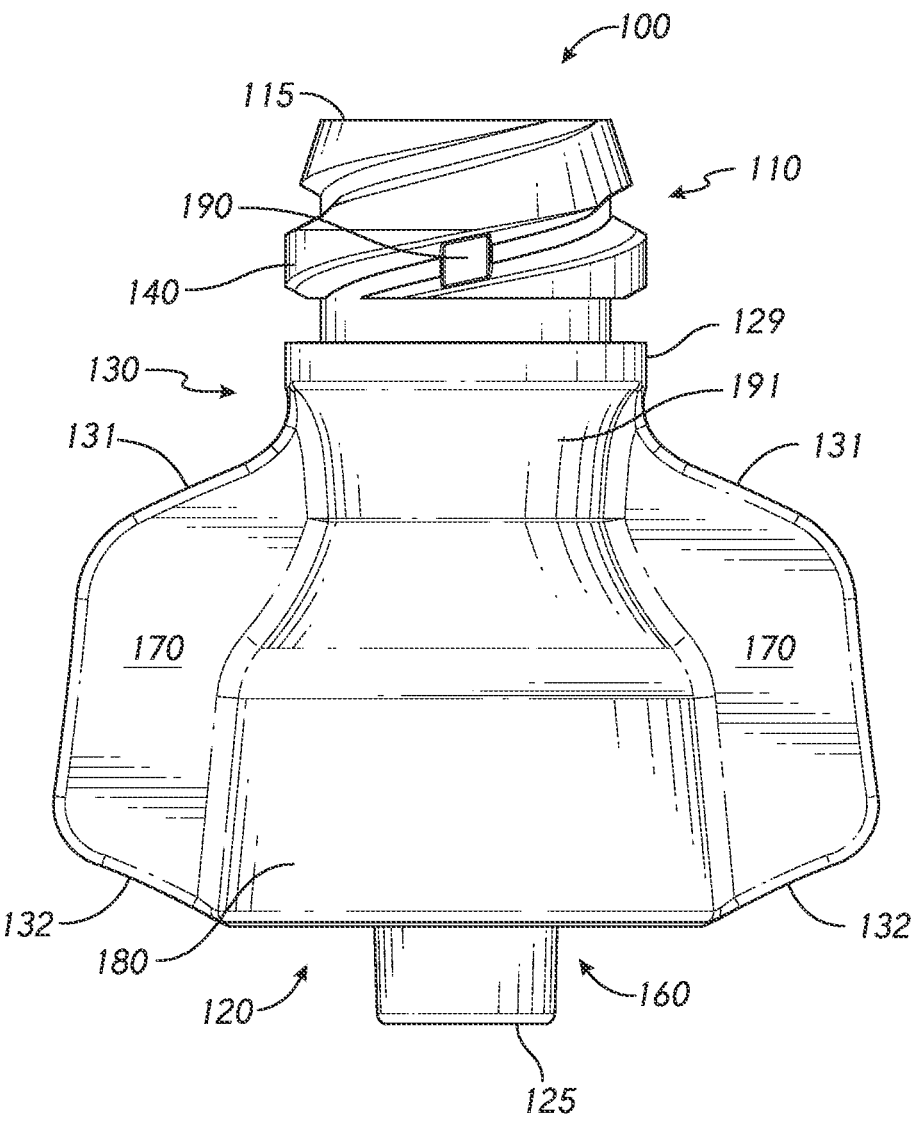
FIG. 1A is a front view of another embodiment of a medical connector that is configured to receive one or more emitters of one or more therapeutic agents.

As illustrated in FIG. 1A, in some embodiments the grasping portion 170 can comprise one or more upper edges 131 and/or one or more lower edges 132. As shown, one or both of the upper edges 131 can be slanted, such as with a downwardly sloped slant; and/or one or both of the lower edges 132 can be slanted, such as with an upwardly sloped slant. In an intermediate region of the connector 100 (e.g., below the thread-stop or collar 129 and above the distal region 120), the connector body can comprise a first region having a first cross-sectional width or diameter, a second region positioned distal from the first region and having a second cross-sectional width or diameter, and a third region positioned distal from the second region and having a third cross-section width or diameter. As shown in FIG. 1A, the second cross-sectional width or diameter can be smaller than either or both of the first cross-sectional width or diameter and/or the third cross-sectional width or diameter. As shown, in a region of the connector body below the second region, the connector body can comprise a continuously increasing outer cross-section or diameter that produces an outward flare from the second region in a distal direction toward the distal region 120 of the connector 100.

As shown in FIG. 1A, in some embodiments one or more friction-inducing impediments 190 can be positioned circumferentially along the connection structure 140 in a region that is generally about midway between the grasping portions 170. In some embodiments, such as shown in FIG. 1, the friction-inducing impediment 190 can be positioned circumferentially along the connection structure 140 in general alignment with one or more longitudinal edges of one or more grasping portions 170 (see FIG. 2).

In some embodiments (not shown), the horizontal cross-sectional width of the grasping portion 170 is no larger than the external diameter or horizontal cross-sectional width of the base portion 180, and/or may comprise one or more small friction-inducing structures, such as one or more protrusions, grooves, and/or other slide-resistant structures or materials. In some embodiments, the grasping portion 170 can be omitted, as with any other feature, structure, material, or step disclosed or illustrated in this specification.

In some embodiments, all or a portion of the fluid pathway 135 inside of the connector 100 can be straight, as illustrated in FIG. 3A (either before or after insertion of an emitter 200, as shown in FIGS. 3B and 3C), from the proximal region 110 or proximal end 115 to the distal region 120 or end 125 of the connector 100, such that a single straight line can be drawn within the fluid pathway 135 from the beginning to the end of the fluid pathway 135. In some embodiments, the fluid pathway 135 can extend along a generally straight path without one or multiple sharp, angular, perpendicular, and/or obtuse changes in direction in the fluid pathway 135. In some embodiments, the fluid pathway 135 is straight or generally straight at least along a majority of the longitudinal length of the fluid pathway 135. The fluid pathway 135 can be straight or generally straight along any particular segment of the fluid pathway, such as along the distance between all or a majority of the proximal end 115 of the connector 100 and the proximal end of the intermediate region 192, between all or a majority of the proximal end of the intermediate region 192 and the distal end of the intermediate region 192, and/or between all or a majority of the proximal end of the portion of the fluid pathway 135 within the male protrusion 160 and the distal end of the portion of the fluid pathway 135 within the male protrusion. A straight path or a generally straight path can diminish turbulence and/or stagnation in one or more portions of the fluid pathway 135 and/or can provide a high flow rate and low fluid resistance.

As shown in FIG. 3A, the diameter or horizontal cross sectional width of the fluid pathway 135 can vary along the longitudinal length of the fluid pathway 135. For example, as illustrated in FIG. 3A, the diameter or cross sectional width of the fluid pathway 135 in at least a portion of the proximal region 110 can be larger than the diameter or cross sectional width of the fluid pathway 135 in at least a portion of an intermediate region 192, which in turn can be larger than the diameter or cross sectional width of the fluid pathway 135 in at least a portion of the distal region 120, such as the portion of the fluid pathway 135 inside of the male protrusion 160.

In some embodiments, as shown, the connector 100 can comprise a stationary structure without any moving external and/or internal parts during use. For example, the external and/or internal shape, orientation, position, and/or size of the connector 100 and its internal components before attachment to or engagement with another medical device can be the same as it is after attachment to or engagement with another medical device. In some embodiments, the connector 100 can comprise moving parts to facilitate connection and disconnection, opening and closing of the connector to form a valve, and/or regulation of pressure or volume.

The connector 100 can comprise one or more additional features that are not shown in FIGS. 1-7, such as proximal and/or distal ends 115, 125 that include resealably openable and closeable apertures with one or more resilient or rigid sealing elements to enable selective fluid flow; a rigid internal cannula or support member or spike that is configured to assist in supporting or opening a sealing element; a body 130 that is clear or transparent or includes a clear or transparent portion and/or one or more other internal structures that are clear or transparent or include a clear or transparent portion that is or are configured to enable viewing of fluid within the internal fluid pathway 135 during use; a cap for selectively closing the fluid pathway; and/or a pressure-regulating or volume-regulating feature inside of the connector 100 to enable neutral flow, etc. For example, any feature, structure, material, component, or step illustrated or described in any embodiment of U.S. Pat. Nos. 5,685,866; 7,815,614; 8,454,579; and/or 8,758,306, which are each incorporated by reference herein in their entireties, can be used with or instead of any feature, structure, material, component, or step illustrated or described in any embodiment in this specification.

In some embodiments, as shown, the connector 100 can be configured to receive or include one or more components that are configured to provide one or more therapeutic agents into the medicinal fluid that is inside and/or moving through the fluid pathway 135. For example, as illustrated in FIGS. 3B, 3C, and 6B, an emitter 200 of one or more therapeutic agents can be inserted into the connector 100 in an internal region, such as in the intermediate region 192, of the fluid pathway 135. As illustrated, in some embodiments, the emitter 200 is positioned entirely within the connector 100 and not partially or entirely positioned within another medical device, such as a syringe. The connector 100 can be temporarily or permanently attached to a syringe or any other medical device. The connector 100 with the emitter 200 can be configured to provide infusion of one or more therapeutic agents in a low-profile, non-bulky, inexpensive manner, without requiring large or complex storage or logistical requirements.

The emitter 200 can comprise any material and/or structure that is configured to provide, leach out, release, diffuse, infuse, dissolve, erode into, or otherwise emit a therapeutic agent into the fluid pathway 135, alone or in combination with fluid flowing through the fluid pathway 135. In some embodiments, the emitter 200 can comprise a non-dissolving substrate or storage material or matrix or other base material in which a therapeutic agent is temporarily held or captured or bound until the therapeutic agent is emitted within the fluid pathway 135. The emitter 200 can have any suitable shape. For example, the emitter 200 can be cylindrical (as shown) or rectangular. In some embodiments, as shown, the emitter 200 can be elongate (e.g., its longitudinal length, from its proximal end 201 or face to its distal end 203 or face is larger than its diameter or cross sectional area). As illustrated, some emitters 200 are solid or substantially solid or resistive to fluid flow from a proximal end or face 201 to a distal end or face 203. For example, as shown, in some embodiments there are no internal, discrete, and/or generally longitudinally oriented fluid pathways within or through the emitter 200; rather, fluid may be permitted to soak into or be absorbed by or pass through the emitter 200 only in essentially random or highly tortious directions (e.g., not a direct or discrete pathway), and/or fluid may not be permitted to soak into or pass through the emitter 200 at all. In some embodiments (not shown), an emitter 200 for use with the connector 100, or with any other embodiment of a connector, can include one or more apertures, channels, tunnels, passages, and/or fluid pathways that are configured to carry or convey fluid through or within the emitter (e.g., from a proximal end or face 201 to a distal end or face 203) without substantial resistance to fluid flow.

In some embodiments, all or at least a portion of the outer housing of the connector 100 where all or at least a portion of the emitter 200 is contained can be clear or transparent to permit viewing of the emitter 200 from outside of the connector 100. In some embodiments, as shown, the emitter 200 is very small. For example, as shown in FIG. 3a, the longitudinal length of the emitter 200, from its proximal face to its distal face can be less than or equal to about the longitudinal length of the conduit 155 within the proximal region 110 and/or less than or equal to about the longitudinal length of the male protrusion 160; and/or the diameter or cross-sectional area of the emitter 200 can be less than or equal to about the outer diameter of the male protrusion 160. In some embodiments, the longitudinal length of the emitter 200 and/or the diameter of the emitter can be a few millimeters (e.g., at least about 2 millimeters or at least about 4 millimeters). Many other sizes and shapes and configurations can be used for the emitter 200.

As illustrated, in some applications, the emitter 200 can comprise a compressible and/or fibrous matrix material on which a therapeutic agent has been coated or into which a therapeutic agent has been infused, impregnated, soaked, absorbed, and/or bonded. In some embodiments, the emitter 200 can include any suitable biocompatible binder to facilitate a temporary water-soluble or other liquid-soluble bond between the base material and the therapeutic agent, or the emitter 200 may not include any binder. In some embodiments, the emitter 200 does not include a substrate but is instead formed of a consumable material that gradually erodes away or dissolves into the fluid pathway 135 during infusion until it is used up. Any type of therapeutic agent can be used, including but not limited to one or more nourishing agents (e.g., vitamins, minerals, etc.), pain-diminishing medications, antibiotics, antimicrobials (e.g., any chlorhexidine-based compound), anti-inflammatories, sedatives, anticoagulants (e.g., heparin), chemotherapy drugs, and/or other types of therapeutic agent. The size and shape of the emitter 200 and/or of the overall connector 100 can be very different depending upon the amount or type of therapeutic agent that is intended to be infused. For example, a very large connector can be used when a large amount of therapeutic agent needs to be infused. Many other different types of emitters can be used instead of or in addition to the emitter 200 as illustrated. For example, an emitter can be provided in the form of a coating on an interior surface of the connector 100 or a material integrated into a portion of the base of the body 130 of the connector 100, or any other suitable material or structure that provides a therapeutic agent at a desired time, in a desired dosage, and/or at a desired infusion rate. Among many other embodiments, an emitter for use with the connector 100 can be provided in the form of any of the cartridges or other emitters that are illustrated or described in International PCT Publication No. WO2013/023146 A1 (Di Fiore), which is incorporated by reference herein in its entirety. Many other types of emitters can be used instead of or in addition to those illustrated or described.

In some embodiments in which an emitter 200 is provided in the form of an inserted material, such as is shown in the example of FIG. 3B, the interior region of the connector 100 can comprise a retaining structure 210 for the emitter 200, as illustrated in FIG. 3A. Although the retaining structure 210 is illustrated with particular dimensions and features, the retaining structure 210 can comprise any suitable material or structure that retains the emitter 200 in such a way that the emitter 200 can be configured to emit one or more therapeutic agents as desired for a particular medical therapy.

As illustrated, in some examples, the retaining structure 210 can comprise one or more retaining components 230 that extend from an internal wall of the connector 100 into an internal space of the connector (such as radially inwardly). For example, as shown, the retaining components 230 can be retaining struts that extend generally longitudinally along the fluid pathway 135. The retaining components 230 can be positioned in the intermediate region 192, as shown. In some embodiments, the retaining structure 210 can comprise at least two or at least three or at least four (as shown in FIG. 6B) retaining components 230 such as retaining struts. As shown in FIG. 7C, one or more of the retaining components 230 can comprise a first portion or component that extends a first distance from an internal wall of the connector 100 into an internal space of the connector and a second portion or component that extends a second distance from an internal wall of the connector 100 into an internal space of the connect. The second distance can be greater than the first distance. For example, one or more of the retaining struts can comprise a retaining protrusion, such as an elongate longitudinal portion, and a base portion 240. The longitudinal portion can be formed as a protrusion extending radially inwardly from the interior wall of the intermediate region 192 of the fluid pathway 135 of the connector 100. As shown, in some embodiments, one or more of the base portions 240 can be radially aligned with one or more of the longitudinal portions 230. One or more of the base portions 240 can extend radially inwardly from the interior wall of the fluid pathway 135 further than one or more of the longitudinal portions 230, as illustrated in FIGS. 3A-3C, 6A, 7A, and 7C, for example.

In some embodiments, as shown, the retaining structure 210 can provide a retaining space within which the emitter 200 can be retained. For example, the retaining space can correspond to the outer width or thickness of the emitter 200, such as by being about the same size as or slightly smaller than the outer width or thickness of the emitter 200. When an emitter 200 is inserted into a retaining space, such as by pushing the retainer into the proximal end 215 of the connector 100, through the proximal portion of the fluid pathway 135, and into the intermediate portion 192, the emitter 200 can radially compress or contract by a small amount such that the retaining structure 210 can exert a radially inwardly directed retaining force against the emitter 200 that is sufficient to produce an increase in friction that resists dislodgment of the emitter 200 from the retaining space (for example, as shown in FIG. 6C). In some embodiments, as illustrated, the emitter 200 can be securely retained within the connector 100 in a manner that resists or prevents either or both of longitudinal or lateral movement of the emitter 200 within the retaining space. In some embodiments (not shown), the retaining space is configured to be somewhat larger than the emitter 200 to permit the emitter 200 to move or float within the retaining space, either before or during infusion.

As shown, a plurality of longitudinal portions 230 can be positioned radially around the retaining space such that the plurality of longitudinal portions 230 are configured to contact the outer surface of the emitter 200 when inserted. In some embodiments, as illustrated, the longitudinal portions 230 are provided generally equally spaced circumferentially from each other. As illustrated, one or more of the longitudinal portions can comprise longitudinal faces (e.g., facing radially inwardly) that are slightly inwardly tapered along the longitudinal dimension in the proximal-to-distal direction, such that the distance between respective longitudinal portions is slightly less on the distal side of the longitudinal portions than on the proximal side of the longitudinal portions. This inward tapering can help to securely retain the emitter 200 when inserted into the retaining space. As shown in FIG. 7C, one or more of the longitudinal portions 230 can include a proximal face or region 260 that is tapered or beveled or slanted to facilitate insertion of an emitter 200 into the retaining space by providing an initially wide but gradually narrowing region for the emitter 200 upon insertion of the emitter 200 into the retaining space.

As shown in FIGS. 6B and 8, a flow space 250 can be provided between two or more retaining components (e.g., longitudinal portions 230) sequentially positioned circumferentially around the fluid pathway 135 (and/or generally surrounding or positioned generally around the retaining space). As shown in FIGS. 8 and 8A, the one or more flow spaces 250 can be configured to permit fluid flowing through the fluid pathway 135 within the connector 100 to flow around the longitudinal portions 230 and through the flow spaces 250, along one or more lateral sides or lateral surfaces of the emitter 200, such as between the one or more lateral sides or lateral surfaces of the emitter 200 and the internal wall of the fluid pathway 135. In some embodiments, there is at least one flow space 250, or at least two flow spaces 250, or at least four flow spaces 250 (as shown). In some embodiments, as illustrated in FIG. 8, at least a majority of the external surface area of the emitter 200 is spaced from the internal surface of the fluid pathway 135 so that the fluid pathway 135 can pass adjacent to and around the outside of the emitter 200 to permit some or all of the fluid to flow around the outside of the emitter 200 (e.g., at least a majority of the external lateral surface area of the emitter 200 does not contact one or more retaining components or other surfaces inside of the connector 100). In some embodiments of connector 100, there are no flow spaces or only very small and/or very constricted flow spaces, such that all or a majority of the fluid pathway and the fluid flowing through the connector is configured to pass within or through the emitter 200 (e.g., by passing through a proximal portion or face 201 of the emitter 200 and exiting out of a distal portion or face 203 of the emitter 200). Such an emitter 200 can have many forms; for example, it can be solid and/or porous and/or include one or more apertures, channels, tunnels, passages, and/or fluid pathways for conveying or carrying fluid.

A base retainer can be formed in any suitable manner, such as by a plurality of base portions 240 (as illustrated), that can provide a lower flow space 280 between a distal end of the intermediate region 192 and a distal end of the emitter 200, as shown in FIGS. 3C and 8. The distal end of the retaining space, as shown, can include an aperture 270 that is smaller in diameter than another portion of the flow pathway 135 in the intermediate region 192 and/or that is smaller in diameter than the retaining space. Within the flow pathway 135, the aperture 270 can lead from the intermediate region 192 to the interior of the male protrusion 160, as illustrated. The base retainer can assist in retaining the emitter 200 apart or spaced away from the distal end of the intermediate region and/or from the aperture 270, so as to enable fluid flowing through the fluid pathway 135 to flow around the distal end of the emitter 200 and out of the aperture 270 (without causing the emitter 200 to plug up or block the aperture 270).

In some embodiments, as shown in FIG. 7C, the circumference of a circle transcribed by the longitudinal portions 230 and/or the base portions 240 of the retaining structures 210 around the fluid path can be greater than the circumference of the internal fluid pathway 135 of the distal end 125 (and/or greater than the circumference of the aperture 270 of the fluid pathway of the distal end 125). In some embodiments, as shown in FIG. 7C, the distance across the intermediate region 192 between generally opposite facing longitudinal portions 230 and/or base portions 240 can be greater than a minimum diameter of the internal fluid pathway 135 of the distal end 125 and/or greater than the diameter of the aperture 270 of the fluid pathway of the distal end 125. For instance, as shown in FIG. 7C, in some embodiments, where two retaining structures are positioned generally opposite one another about a circumference formed by the retaining structures 210 around the fluid path, the transverse distance between the oppositely positioned retaining structures 210 and/or base portions 240 is greater than the diameter of the internal fluid pathway 135 of the distal end 125 (and/or greater than a diameter of the aperture 270). As shown in FIGS. 6B and 6C, respectively, in some embodiments, the circumference formed by the retaining structures 210 around the fluid pathway is about the same size or just smaller than the circumference of an emitter 200. In some embodiments, when the circumference formed by the retaining structures 210 around fluid pathway is just smaller than the circumference of an emitter 200, the longitudinal portions 230 of the retaining structures 210 can engage (e.g., hold or restrain) the emitter 200 (e.g., by friction). In some embodiments, as shown in FIG. 7C, when the internal fluid pathway 135 is smaller than the portion of the intermediate region 192 between the longitudinal portions 230, then a distal shelf or support region or fluid diverting region can be formed in the internal region 192 between the longitudinal portions and the internal fluid pathway 135 of the distal end 125. As shown in FIG. 7C, the shelf or support region or fluid diverting region can be generally horizontal or generally transverse in some embodiments.

In some embodiments, as shown in FIGS. 6A and 7C, a circumference formed by the base portions 240 about the fluid path within the the of the intermediate region 192 can be greater than the circumference of the internal fluid pathway 135 of the distal end 125 (and/or greater than the circumference of the aperture 270 of the fluid pathway of the distal end 125). For instance, as shown in FIG. 7C, in some embodiments, where two base portion 240 structures are positioned generally opposite from one another about a circumference formed by the base structures 240 around the fluid path, the transverse distance between the oppositely positioned retaining structures 210 is greater than the diameter of the internal fluid pathway 135 of the distal end 125 (and/or greater than a diameter of the aperture 270). As shown in FIG. 7C, in some embodiments, the internal-most circumference formed by the base portions 240 terminates circumferentially outwardly of the circumference of the aperture 270. In some embodiments, as shown in FIG. 3A, the portion of the intermediate region 192 within the longitudinal portions 230 is smaller in transverse width or diameter or circumference than the conduit 155 within the proximal region 110.

As illustrated in FIGS. 8 and 8A, the connector 100 can be configured so that the position and orientation of the retaining structure and the emitter 200 permits fluid flowing through the fluid pathway 135 to flow mostly or entirely around and/or outside of the emitter 200. In its initial state, the emitter 200 can be dry or not saturated with fluid. As fluid flows around and/or outside of the emitter 200, the emitter 200 is wetted or the level of wetness of the emitter 200 is increased and therapeutic agent is emitted from the emitter 200 into the flowing fluid, first from the periphery of the emitter 200 (which is closest to the flowing fluid) and then from the core or interior of the emitter 200. As the fluid flowing around the emitter 200 soaks into and/or eventually saturates the emitter 200, therapeutic agent contained within the interior of the emitter 200 migrates toward the periphery of the emitter 200 and is eventually emitted into the fluid pathway 135. By directing the fluid flow predominantly around and/or outside, rather than predominantly through, the emitter 200, the connector 100 does not become plugged up or require excessive force on the syringe to accomplish fluid infusion. In some embodiments (not shown), most or all of the fluid flow can be directed through the emitter 200, for example in embodiments in which there are no flow spaces 250, 280. Also, by directing the fluid flow predominantly around and/or outside, rather than predominantly through the emitter 200, the connector 100 allows at least a portion of fluid to flow freely through the connector.

As shown in the example of FIG. 8, in some embodiments, the proximal face of the emitter 200 can be unobstructed by the retaining structure 210 within the fluid pathway 135. For example, as shown, the retaining structure 210 can be positioned only on or along or in contact with one or more outer lateral or longitudinal sides of the emitter 200 and/or not on or along or in contact with or in blocking relationship with a proximal face of the emitter 200. In some embodiments, the proximal face of the emitter 200 is exposed to the full diameter or cross-sectional width of the fluid pathway 135 of the conduit 155 within the proximal region 110, such that the fluid flowing through the fluid pathway is configured to initially contact the full proximal face of the emitter 200 when flowing in a distally directed longitudinal direction, without being required to twist or turn to contact the proximal face of the emitter 200. In some embodiments, as illustrated in FIG. 8, there is no constriction or blockage of the fluid pathway 135 within the proximal region 110 between the conduit 155 and the proximal face of the emitter 200.

The emitter 200, in some implementations, can be positioned within the fluid pathway 135 a sufficient distance from the proximal end 115 of the connector 100 that when a male protrusion (such as from a syringe) is inserted into the proximal region 110 of the connector, the distal end of the male protrusion does not contact the emitter 200.

In some embodiments, as illustrated, the portion of the fluid pathway 135 located within the male protrusion 160 can be generally or completely unobstructed and/or unimpeded. For example, as shown, the emitter 200 can be located entirely outside of the fluid pathway 135 located within the male protrusion 160. For example, the emitter 200 can be configured to be positioned within the intermediate portion 192 of the connector 100, as shown. In some embodiments, as illustrated, the emitter 200 can be positioned entirely inside of the connector 100, with no portion of the emitter protruding outside of the connector 100. As shown in FIGS. 8 and 8A, the connector can be shaped, structured, and/or contoured such that the fluid pathway 135 of the connector 100 can be configured to convey liquid along a first portion of the fluid pathway 135 around the outside of the emitter 200, the first portion having an outer perimeter that is wider than the diameter of the emitter 200, and along a second portion of the fluid pathway 135 in a distal direction from the emitter 200 into a region having an outer perimeter that is narrower than the diameter of the emitter 200 (e.g., inside of the male protrusion 160).

The connector 100 can be used in many different ways and/or in many different systems for providing one or more therapeutic medical effects. An example of using the connector 100 in a method of providing an anti-microbial block in a patient standby fluid line or providing an emitted therapeutic agent (such as any agent disclosed elsewhere in this specification) in any fluid line can include one or more of the following steps, and/or one or more instructions can be provided to the user (e.g., healthcare practitioner or patient) to perform one or more of the following steps, in any suitable order:

(1) The connector 100 with an antimicrobial emitter 200 or another type of emitter 200 of one or more therapeutic agents can be attached to the proximal end of a fluid line at the end of an infusion stage to initiate the beginning of a standby stage. In some embodiments, the emitter 200 can comprise a dry or unsaturated, biocompatible, clinically safe dosage of an anti-microbial material, such as a chlorhexidine compound, or an anti-thrombotic material, or any other therapeutic material, that is configured to be infused into the fluid pathway 135. A standard liquid, such as water or saline, or any other suitable liquid, can be forced into or infused into the proximal end 115 of the connector 100 from another medical device, such as a syringe or a pump or a vial or a fluid line or an IV bag, and brought into fluid communication with the emitter 200 (e.g. by passing around or through, and/or within it).

(2) An antimicrobial or other therapeutic agent can be automatically emitted from the emitter 200 and infused into the fluid line to form an antimicrobial block downstream of the emitter 200 and/or to provide any other therapeutic effect in the fluid line. In some embodiments, only a small amount of standard or other liquid is passed from the syringe into the connector 100 (e.g., less than or equal to about 10 cc or less than or equal to about 20 cc or less than or equal to about 50 cc of water or saline), such that the antimicrobial or other agent remains in the fluid line during the standby stage and does not migrate in any appreciable amount into the patient's bloodstream.

In some embodiments, by utilizing connectors 100 with antimicrobial-infused emitters 200 or other therapeutic-agent-infused emitters 200, a health clinic or hospital can conveniently diminish the space, expense, and logistics associated with providing and infusing antimicrobial liquid or other therapeutic liquid into fluid lines to perform anti-microbial blocks. The connector 100 can be used in many different types of methods.

In some embodiments, as shown, the medical connector 100 is not a valve. In some embodiments, the medical connector 100 does not have a dynamic sealing mechanism. In some embodiments, for example, the medical connector 100 does not have both a closed mode (a position where fluids do not pass and/or are restricted through the medical connector 100) and an open mode (a position where fluids pass through the medical connector 100 freely). In some embodiments, the medical connector 100 is not configured to stop the flow of fluid through the medical connector 100. In some embodiments, the medical connector is not config-ured to provide a low pressure seal. In some embodiments, the medical connector lacks a closable aperture. In some embodiments, the medical connector 100 is open. In some embodiments, fluid can flow freely (and/or in unrestricted fashion) through the proximal end 115, to the intermediate region 192, and through the distal region 120 via the internal fluid pathway 135 (e.g., when the medical connector 100 lacks or has an emitter 200). In some embodiments, the medical connector 100 lacks a ring seal around the fluid path and in the intermediate region.

In some embodiments, the internal fluid pathway 135 of the medical connector 100 does not have a stretchable and/or compressible gland or resilient seal. In some embodiments, the internal fluid pathway 135 of the medical connector 100 is not configured to receive a stretchable and/or compress-ible gland or resilient seal. In some embodiments, the medical connector 100 is not configured to allow the com-pression of a stretchable and/or compressible gland or resilient seal within the internal fluid pathway 135. In some embodiments, the medical connector 100 lacks an actuator configured to open and close. In some embodiments, the medical connector 100 lacks a rigid supporting or centering or piercing member (e.g., a cannula, needle, spike, etc.). In some embodiments, the internal fluid pathway 135 lacks a rigid member. In some embodiments, the medical the inter-mediate portion 192 is not configured to allow a rigid member to pass into the intermediate portion 192. In some embodiments, the base portions 240 do not extend into the internal fluid pathway 135 of the distal end 125. In some embodiments, the fluid pathway 135 in the distal region 120 is of insufficient diameter to accommodate a rigid member.

Any terms generally associated with circles, such as "radius" or "radial" or "diameter" or "circumference" or "circumferential" or any derivatives or similar types of terms are intended to be used to designate any corresponding structure in any type of geometry, not just circular structures. For example, "radial" as applied to another geometric struc-ture should be understood to refer to a direction or distance between a location corresponding to a general geometric center of such structure to a perimeter of such structure; "diameter" as applied to another geometric structure should be understood to refer to a cross sectional width of such structure; and "circumference" as applied to another geo-metric structure should be understood to refer to a perimeter region. Nothing in this specification or drawings should be interpreted to limit these terms to only circles or circular structures.

The following is claimed:

1. A method of enabling a user to attach a medical connector having an emitter of one or more therapeutic agents to both a syringe and a resealable female luer connector on a fluid line at the same time, the method comprising:
providing a medical connector with a housing and an internal fluid pathway, the housing comprising:
a proximal region with a proximal screw thread sur-rounding an open female end of the housing, the proximal screw thread comprising at least one dis-connection-resistant structure comprising: (a) a pro-trusion between respective thread turns, the protru-sion extending radially outwardly farther than an inner surface between the respective thread turns, or (b) a radially outwardly flared thread portion in a threaded region that has a larger outermost diameter than another thread portion;
an intermediate region configured to retain an emitter of one or more therapeutic agents; and
a distal region without any threads, the distal region comprising a male protrusion, the male protrusion having a diameter on a distal end that is wider and a length that is shorter than a standard luer, but the male protrusion still being configured to fit tightly within a luer opening of the resealable female luer connector;
wherein the internal fluid pathway is open from the proximal region to the distal region without a dynamic seal;
instructing a user to attach the medical connector to the syringe; and
instructing the user to attach the medical connector to the resealable female luer connector;
whereby the attachment between the syringe and the medical connector is secure and resistant to disconnec-tion, whereas the attachment between the medical con-nector and the resealable female luer connector is temporary and non-secured.

2. A medical fluid connector configured to receive an emitter of therapeutic agents to be emitted into a fluid pathway within the medical fluid connector, the medical fluid connector comprising:
a proximal end configured to be coupled to a syringe, the proximal end comprising threading and one or more disconnection-resisting structures disposed along a por-tion of the threading, the threading configured to facili-tate coupling the proximal end to the syringe, and the one or more disconnection-resisting structures config-ured to contact threading of the syringe to increase friction between the threading of the proximal end and the threading of the syringe to resist decoupling of the proximal end and the syringe;
a threadless distal end configured to be coupled with a female connector, the threadless distal end being over-sized compared to a distal end of a standard luer connector such that the threadless distal end penetrates to a lesser depth within an opening of the female connector compared to the distal end of the standard luer connector, wherein a fluid pathway from the proxi-mal end to the threadless distal end is configured to direct fluid from the syringe to the female connector; and
one or more grasping portions disposed between the proximal end and the threadless distal end, the one or more grasping portions configured to facilitate a user threading the proximal end and the syringe together such that the one or more disconnection-resisting struc-tures of the proximal end contact the threading of the syringe thereby increasing the friction between the threading of the proximal end and the threading of the syringe to resist decoupling of the proximal end and the syringe.

3. The medical fluid connector of claim 2, wherein the one or more disconnection-resisting structures comprise one or more protrusions.

4. The medical fluid connector of claim 2, wherein the one or more disconnection-resisting structures comprise an enlarged thread portion.

5. The medical fluid connector of claim 2, wherein the one or more disconnection-resisting structures are disposed between thread turns of the threading of the proximal end.

6. The medical fluid connector of claim 2, wherein the one or more disconnection-resisting structures extend radially outward from an inner surface of the threading of the proximal end to a position that is radially inward of a radially outermost surface of the threading of the proximal end.

7. The medical fluid connector of claim 2, wherein the threading of the proximal end comprises an outermost diameter that increases in size in a proximal to distal direction to help resist decoupling of the syringe and the proximal end.

8. The medical fluid connector of claim 2, wherein the threadless distal end is configured to help facilitate a non-secured, temporary attachment to the female connector.

9. The medical fluid connector of claim 2, wherein the one or more grasping portions comprise one or more tabs.

10. The medical fluid connector of claim 2, wherein lengths of the one or more grasping portions in a proximal-distal direction are more than half of an overall length of the medical fluid connector in the proximal-distal direction.

11. A medical fluid connector configured to receive an emitter of therapeutic agents to be emitted into a fluid pathway within the medical fluid connector, the medical fluid connector comprising:

a proximal end configured to be coupled to a syringe, the proximal end comprising threading and one or more disconnection-resisting structures disposed along a portion of the threading, the threading configured to facilitate coupling the proximal end to the syringe, and the one or more disconnection-resisting structures configured to contact threading of the syringe to increase friction between the threading of the proximal end and the threading of the syringe to resist decoupling of the proximal end and the syringe; and one or more grasping portions, the one or more grasping portions configured to facilitate a user threading the proximal end and syringe together such that the one or more disconnection-resisting structures of the proximal end contact the threading of the syringe thereby increasing the friction between the threading of the proximal end and the threading of the syringe to resist decoupling of the proximal end and the syringe;

an oversized distal end compared to a distal end of a standard luer connector such that the oversized distal end penetrates to a lesser depth within an opening of a female connector compared to the distal end of the standard luer connector.

12. The medical fluid connector of claim 11, wherein a fluid pathway from the proximal end to the distal end is configured to direct fluid from the syringe to the female connector.

13. The medical fluid connector of claim 12, wherein the distal end is configured to help facilitate a non-secured, temporary attachment to the female connector.

14. The medical fluid connector of claim 11, wherein the one or more disconnection-resisting structures comprise one or more protrusions.

15. The medical fluid connector of claim 11, wherein the one or more disconnection-resisting structures comprise an enlarged thread portion.

16. The medical fluid connector of claim 11, wherein the one or more disconnection-resisting structures are disposed between thread turns of the threading of the proximal end.

17. The medical fluid connector of claim 11, wherein the one or more disconnection-resisting structures extend radially outward from an inner surface of the threading of the proximal end to a position that is radially inward of a radially outermost surface of the threading of the proximal end.

18. The medical fluid connector of claim 11, wherein the threading of the proximal end comprises an outermost diameter that increases in size in a proximal to distal direction to help resist decoupling of the syringe and the proximal end.

19. The medical fluid connector of claim 11, wherein the one or more grasping portions comprise one or more tabs.

20. The medical fluid connector of claim 11, wherein lengths of the one or more grasping portions in a proximal to distal direction are more than half of an overall length of the medical fluid connector in the proximal to distal direction.

21. A method of disposing a medical fluid connector configured to receive an emitter of therapeutic agents in a fluid infusion line, the method comprising:

connecting a proximal end of the medical fluid connector to a syringe by way of a threaded connection, wherein the medical fluid connector comprises one or more grasping portions extending radially outward to facilitate a user's threading of the proximal end and syringe together such that one or more disconnection-resisting structures of the proximal end contact threading of the syringe, thereby increasing friction between threading of the proximal end and threading of the syringe to resist disconnection of the proximal end and the syringe; and coupling a threadless distal end of the medical fluid connector with a female connector by way of inserting the threadless distal end of the medical fluid connector into an opening of the female connector such that a fluid pathway extends from the syringe through the medical fluid connector and to the female connector, the threadless distal end being oversized as compared to a distal end of a standard luer connector such that the threadless distal end penetrates to a lesser depth within an opening of the female connector compared to the distal end of the standard luer connector.

* * * * *